(12) United States Patent
Zussman et al.

(10) Patent No.: US 8,546,333 B2
(45) Date of Patent: Oct. 1, 2013

(54) ALBUMIN FIBERS AND FABRICS AND METHODS OF GENERATING AND USING SAME

(75) Inventors: Eyal Zussman, Haifa (IL); David Simhon, Ramat-Efal (IL); Shmuel Chervinsky, Haifa (IL); Abraham Katzir, Tel-Aviv (IL); Zvi Nevo, Herzlia (IL); Yael Dror, Misgav (IL)

(73) Assignee: Technion Research & Development Foundation Limited, Haifa (IL)

( * ) Notice: Subject to any disclaimer, the term of this patent is extended or adjusted under 35 U.S.C. 154(b) by 728 days.

(21) Appl. No.: 12/449,261

(22) PCT Filed: Jan. 31, 2008

(86) PCT No.: PCT/IL2008/000135
§ 371 (c)(1),
(2), (4) Date: Feb. 15, 2010

(87) PCT Pub. No.: WO2008/093342
PCT Pub. Date: Aug. 7, 2008

(65) Prior Publication Data
US 2011/0230411 A1    Sep. 22, 2011

Related U.S. Application Data

(60) Provisional application No. 60/887,621, filed on Feb. 1, 2007.

(51) Int. Cl.
*A61K 38/38* (2006.01)
*C07K 14/76* (2006.01)
*C07K 14/00* (2006.01)
*C12N 5/00* (2006.01)
*A61P 17/02* (2006.01)
*D04H 13/00* (2006.01)

(52) U.S. Cl.
USPC .......... 514/15.2; 530/362; 530/350; 435/398; 442/327; 428/41.1

(58) Field of Classification Search
USPC ................. 514/15.2; 530/362, 350
See application file for complete search history.

(56) References Cited

U.S. PATENT DOCUMENTS 4,576,817 A    3/1986    Montgomery et al.

FOREIGN PATENT DOCUMENTS

| CA | 2595894 | | 8/2006 |
| CN | 1132049 | | 10/1996 |
| CN | 1403163 | * | 3/2003 |
| FR | 877757 | * | 12/1941 |
| IL | WO01/62226 | * | 8/2001 |
| WO | WO 01/80921 | | 11/2001 |
| WO | WO 02/18441 | | 3/2002 |

OTHER PUBLICATIONS

Palmer et al. (Journal of the American Chemical Society, XP002527155, 65: 2187-2190, Nov. 1943).*
Senti et al. (The Journal of Physical Chemistry, vol. 29 (3), 192-211, 1945).*
Briki et al. (Biophysical Journal vol. 83 1774-1788, Oct. 2002).*
The Encyclopedia Britannica (Serum Albumin).*
Zhang (Biomacromolecules, vol. 7, 2006 pp. 1049-1057).*
International Search Report Dated Jun. 15, 2009 From the International Searching Authority Re.: Application No. PCT/IL2008/000135.
Written Opinion Dated Jun. 15, 2009 From the International Searching Authority Re.: Application No. PCT/IL2008/000135.
Barnes et al. "Feasibility of Electrospinning the Globular Proteins Hemoglobin and Myoglobin", Journal of Engineered Fibers and Fabrics, 1(2): 16-29, 2006.
Palmer et al. "The Molecular Structure of Fibers Made From the Native Egg Albumin", Journal of the American Chemical Society, XP002527155, 65: 2187-2190, Nov. 1943.
Senti et al. "Fibrous From Globular Proteins", The Journal of Physical Chemistry, XP002527156, 49(3): 192-196, 1945. 'Preparation of Specimens', p. 195-196, 'Tensile Strength', p. 207-210.
Wnek et al. "Electrospinning of Nanofiber Fibrinogen Structures", Nano Letters, 3(2): 213-216, 2003.
International Preliminary Report on Patentability Dated Aug. 13, 2009 From the International Bureau of WIPO Re.: Application No. PCT/IL2008./000135.
Offica Action Dated Mar. 21, 2011 From the Israel Patent Office Re. Application No. 200106 and Its Translation Into English.
Communication Pursuant to Article 94(3) EPC Dated Dec. 16, 2011 From the European Patent Office Re.: Application No. 08702714.0.
Response Dated Oct. 8, 2010 to Communication Pursuant to Article 94(3) EPC of Apr. 8, 2010 From the European Patent Office Re.: Application No. 08702714.0.
Benarafa et al. "The Ovalbumin Serpins Revisited: Perspective From the Chicken Genome of Clade B Serpin Evolution in Vertebrates", Proc. Natl. Acad. Sci. USA, PNAS, 102(32): 11367-11372, Aug. 9, 2005.
Worthington "Ovalbumin", Worthington Enzyme Manual, Worthington Biochemical Corporation, 1 P., 2010.
Communication Pursuant to Rules 70(2) and 70a(2) EPC and Reference to Rule 39(1) EPC Dated Jul. 30, 2012 From the European Patent Office Re. Application No. 12163748.2.
Examination Report Dated Jul. 20, 2012 From the Australian Government IP Australia Re. Application No. 2008211549.
European Search Report and the European Search Opinion Dated Jun. 21, 2012 From the European Patent Office Re. Application No. 12163748.2.
Communication Pursuant to Article 94(3) EPC Dated Apr. 8, 2010 From the European Patent Office Re.: Application No. 08702714.0.

* cited by examiner

*Primary Examiner* — Anoop Singh
*Assistant Examiner* — Anna Falkowitz

(57) ABSTRACT

Provided are method of generating a fiber from a globular protein such as albumin. Also provided are albumin fibers and fabrics and methods of using same for bonding a damaged tissue or for ex vivo or in vivo formation of a tissue.

3 Claims, 22 Drawing Sheets

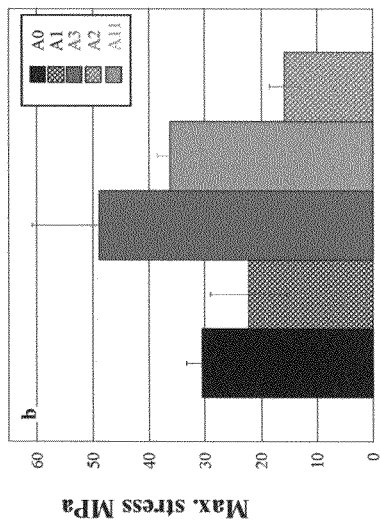
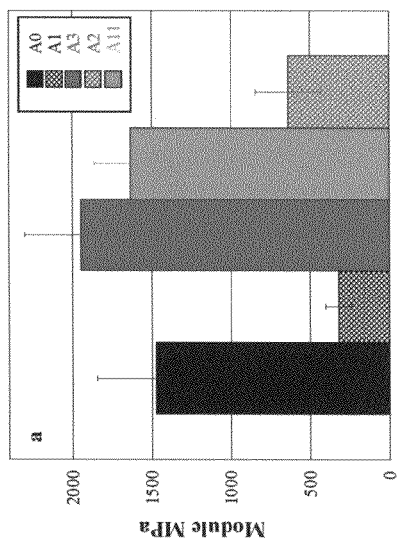
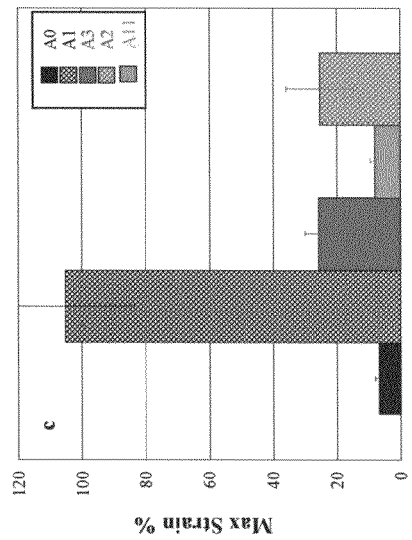

Figs. 20a-e

ALBUMIN FIBERS AND FABRICS AND METHODS OF GENERATING AND USING SAME

RELATED APPLICATIONS

The application is a National Phase Application of PCT Patent Application No. PCT/IL2008/000135 having International Filing Date of Jan. 31, 2008, which claims benefit under 35 U.S.C. §119(e) from U.S. Provisional Patent Application No. 60/887,621, filed on Feb. 1, 2007. The contents of the above Applications are all incorporated herein by reference.

FIELD AND BACKGROUND OF THE INVENTION

The present invention, in some embodiments thereof, relates to albumin fibers and fabrics and, more particularly, but not exclusively, to methods of generating and using same in various therapeutic applications.

Albumin is a globular, water-soluble protein present in both eukaryotic (e.g., human blood and skin) and prokaryotic organisms. It plays a role in stabilizing extracellular fluid volume in the plasma, and serves as a carrier protein for steroids, fatty acids, various cations (e.g., calcium copper, nickel calcium magnesium zinc and mercury), drugs and thyroid hormones.

Human albumin is produced in the liver and is naturally biodegraded by the endothelial system, the muscle, the skin, and the liver. Biodegradation of denatured albumin involves attachment by the gp18 and gp30 scavenger receptors following by digestion in the endosome-lysosome system.

PCT Publication No. WO2005037108 (to Waserman I, Dror M and Simhon D) discloses anastomotic devices (films, sponges, and tubes) fabricated by depositing a mix of albumin and glycerin on a surface.

Albumin was engineered to produce biological glues for bonding biomaterial, supporting sutureless and near-scarless bonding procedures. These include glues activated via light assisted denaturation (Simhon D, et al. Ann Surg 2007; 245: 206-213) or cross-linking reagents such as glutaraldehyde (Bioglue® CryoLife, Inc, Europa, Ltd, UK).

Kirsch A J., et al., J. Urol., 165:574-577, 2001) report the use laser activated albumin to repair congenital anomaly of the male's urethra (hypospadias).

WO0218441 and Gary E Wnek et al., (Nano Lett 3: 213-216, 2003) disclose electrospun fibrin fibers made of fibrin monomer using a solvent such as urea, monochloroacetic acid, or hexafluoroisopropanol (HFIP).

Barnes C P., et al., 2006, disclose electrospinning of hemoglobin using 2,2,2-Trifluoroethanol (TFE) followed by cross linking the electrospun samples with glutaraldehyde. Electrospinning was also performed on collagen, gelatin, elastin and fibrinogen (Li, et al., 2005; McManus, et al., 2006).

U.S. Pat. No. 6,821,479 discloses electrospinning of solution of PEOZ (a polymer: poly(ethyl-oxazoline) which includes 5%-12% albumin.

Additional references include U.S. Pat. No. 7,115,220, WO05098099, WO06137848, U.S. Pat. No. 7,157,428, U.S. Pat. No. 7,166,570, U.S. Pat. No. 6,753,311, U.S. Pat. No. 7,105,229, U.S. Pat. No. 6,989,195 and U.S. Pat. No. 6,638,621.

SUMMARY OF THE INVENTION

The invention in some embodiments provide methods of generating fibers from proteins such as globular proteins and albumin fiber and fabrics, and methods of using same.

According to an aspect of some embodiments of the present invention there is provided a fiber consisting essentially of albumin.

According to an aspect of some embodiments of the present invention there is provided a fiber comprising more than 50% albumin. According to an aspect of some embodiments of the present invention there is provided a composition-of-matter comprising an albumin polymer.

According to an aspect of some embodiments of the present invention there is provided a fiber comprising the composition-of-matter.

According to an aspect of some embodiments of the present invention there is provided an albumin fiber characterized by an elastic modulus of at least 1000 MPa.

According to an aspect of some embodiments of the present invention there is provided an albumin fiber characterized by a tensile stress of at least 20 MPa.

According to an aspect of some embodiments of the present invention there is provided a method of generating a fiber from a globular protein, comprising: (a) dissolving the globular protein into a solution, the solution comprising a reducing agent; and (b) evaporating the solution under conditions suitable for polymerization of the globular protein; thereby generating the fiber from the globular protein.

According to an aspect of some embodiments of the present invention there is provided a method of generating a fiber from a globular protein, comprising: (a) dissolving the globular protein into a solution, the solution comprising a plasticizing agent; (b) extruding the solution in an electric field; and (c) evaporating the solution under conditions suitable for formation of the fiber from the globular protein; thereby generating the fiber from the globular protein.

According to an aspect of some embodiments of the present invention there is provided a fiber formed according to the method of the invention.

According to an aspect of some embodiments of the present invention there is provided a fabric comprising the fiber of the invention.

According to an aspect of some embodiments of the present invention there is provided a fabric formed according to the method of the invention.

According to an aspect of some embodiments of the present invention there is provided a structure coated with the fabric of the invention.

According to an aspect of some embodiments of the present invention there is provided a method of bonding a damaged tissue of a subject, comprising introducing to the damaged tissue of the subject an albumin fabric, thereby bonding the damaged tissue of the subject.

According to an aspect of some embodiments of the present invention there is provided a method of inducing ex vivo formation of a tissue, the method comprising: (i) providing an albumin fabric; and (ii) seeding the albumin fabric with cells in a medium selected suitable for proliferation, differentiation and/or migration of the cells to thereby induce the ex vivo formation of the tissue.

According to an aspect of some embodiments of the present invention there is provided a method of inducing in vivo formation of a tissue, the method comprising: (i) providing an albumin fabric; and (ii) implanting the albumin fabric in a subject to thereby induce the in vivo formation of the tissue.

According to an aspect of some embodiments of the present invention there is provided a fiber formed of a polymer of a globular protein, the globular protein having at least two functional SH groups capable of forming a disulfide bond between two molecules of the globular protein.

According to some embodiments of the invention, the fiber comprising more than 70% albumin.

According to some embodiments of the invention, more than 50% of a structural strength of the fiber results from albumin.

According to some embodiments of the invention, more than 50% of a tensile strength of the fiber results from albumin.

According to some embodiments of the invention, more than 70% of a structural strength of the fiber results from albumin.

According to some embodiments of the invention, more than 70% of a tensile strength of the fiber results from albumin.

According to some embodiments of the invention, wherein substantially all albumin molecules of the polymer are covalently attached to other albumin molecules of the polymer.

According to some embodiments of the invention, the fiber is characterized by an elastic modulus of at least 1000 Mpa.

According to some embodiments of the invention, the fiber is characterized by a tensile stress of at least 20 Mpa.

According to some embodiments of the invention, the method further comprising extruding the solution in an electric field following step (a).

According to some embodiments of the invention, the reducing agent comprises beta-mercapto-ethanol (βME).

According to some embodiments of the invention, the solution comprises a denaturing agent.

According to some embodiments of the invention, the denaturing agent comprises Trifluroethanol (TFE).

According to some embodiments of the invention, the globular protein is albumin.

According to some embodiments of the invention, the conditions comprise presence of oxygen.

According to some embodiments of the invention, the plasticizing agent comprises glycerol.

According to some embodiments of the invention, the solution further comprising a denaturing agent.

According to some embodiments of the invention, the solution further comprising a reducing agent.

According to some embodiments of the invention, the method further comprising forming the fiber into a fabric.

According to some embodiments of the invention, the fabric is non-woven

According to some embodiments of the invention, the fiber or the fabric is attached to a light absorbing agent.

According to some embodiments of the invention, the fiber or the fabric is attached to a drug molecule.

According to some embodiments of the invention, the fiber or the fabric is attached to a plurality of cells.

According to some embodiments of the invention, the method further comprising suturing the albumin fabric to the damaged tissue of the subject.

According to some embodiments of the invention, the method further comprising heat-soldering the albumin fabric to the damaged tissue of the subject.

According to some embodiments of the invention, the cells are stem cells.

According to some embodiments of the invention, the albumin fabric is attached to a drug.

According to some embodiments of the invention, the albumin is modulated by glycerol.

According to some embodiments of the invention, the method further comprising thermally curing the fabric.

According to some embodiments of the invention, the method further comprising plasma treating of the fabric.

According to some embodiments of the invention, the fiber is consisting essentially of albumin.

According to some embodiments of the invention, the at least two functional SH groups being unavailable for forming a disulfide bond in a natural state of the globular protein.

According to some embodiments of the invention, a secondary structure of the globular protein is maintained within the polymer.

According to some embodiments of the invention, about 8-12 molecules of β-mercaptoethanol are provided for each disulfide bond of the protein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9a-c are images of electrospun-based albumin fibers made by electrospinning of solution D. FIG. 9a—a transverse section of albumin-based electrospun fibers; FIG. 9b—One layered albumin-based fabric; FIG. 9c—Four layered albumin-based fabric.

FIG. 10a—Untreated fabric; FIG. 10b—30 seconds exposure; FIG. 10c—120 seconds exposure to plasma etching. Note the albumin fibers surface roughening under prolonged exposure to plasma etching and the formation of perpendicular fissures.

FIG. 11 is a fluorescent image depicting S. aureus containing plasmids with enhanced green fluorescent protein (egfp) reporter gene, over an albumin-based electrospun fabric after the biofilm formation as seen under fluorescence microscopy.

FIG. 12 is a graph depicting S. aureus adhesion to 3 types of biomaterials as monitored by relative fluorescence units (RFU) of enhanced green fluorescent protein (egfp), whose gene was cloned into a plasmid. A statistically significant difference (**) was noted (P<0.05) in the albumin discs compared to the other biomaterials in favor of albumin fabric.

FIG. 13 is a schematic illustration depicting a method of forming an albumin fiber according to some embodiments of the invention. 100—Dissolve albumin in a solution; 110—add a modifier to the dissolved albumin which can increase the efficiency of fiber formation. The modifier may be a denaturing agent, a reducing agent, a plasticizer and/or an agent affecting the pH of the solution; 120—a drug molecule or any moiety of interest can be added to the fiber forming solution or to the formed fiber; 130—evaporation of the solution (the solvent of the protein) for fiber formation. According to some embodiments of the invention this can be done by electrospinning; 140—collect the albumin fiber (e.g., on a collector); 150—forming the fiber into a fabric using e.g., weaving, knitting or non-weaving.

FIG. 14a—untreated open wound. Note the scab formation with migrating inflammatory cells; FIG. 14b—Laser treated (lased) albumin fabric. Note a thin reddish layer of ~12 μm thick (in the magnifying square) containing elongated cells which is made from albumin+ICG fabric and serves as the laser activated biological glue and a ~125 μm thick hyalinized layer which is made of denatured bonded albumin fabric. This fabric imitates a skin graft.

FIGS. 15a-b—Complete reepithelialization of open wound that was treated by a laser soldered albumin; FIGS. 15c-d—partial reepithelialization in the untreated open wound. FIGS. 15a and c—left rim; FIGS. 15b and d—right rims (Magnification×25).

FIG. 16a—Two strips of porcine fascia are made from elongated fascia strip; FIG. 16b—An albumin strip made from solution D and β-mercaptoethanol is placed over the porcine fascia strips in a wet environment and 10% glutaraldehyde is added; FIG. 16c—after two minutes the bonded strips are mounted on an instron loading machine and tested for tensile strength.

FIG. 17 is a scanning electrons microscopy (SEM) image of elecrrospun albumin fibers formed of solution A3 (Table 3; Example 8);

FIGS. 18a-c are graphs depicting the Tensile properties of different albumin fibers. FIG. 18a—Module; FIG. 18b—strength (stress peak); FIG. 18c—extensibility (elongation).

FIG. 19 is a graph depicting typical stress-strain curves of the albumin fibers;

FIGS. 20a-e are images of 2D x-ray diffraction patterns. FIG. 20a—casted film of BSA from solution of 9:1 TFE:H$_2$O and β-ME; FIG. 20b—A1 albumin fibers; FIG. 20c—A3 albumin fibers; FIG. 20d—All albumin fibers; FIG. 20e—A0 albumin fibers.

FIG. 21 is a graph depicting 1D X-ray diffraction patterns after radial averaging.

FIG. 22 is a graph depicting Azymutal intensity of the 10.2 d-spacing (inner) peak.

DESCRIPTION OF SPECIFIC EMBODIMENTS OF THE INVENTION

The present invention, in some embodiments thereof, relates to albumin fibers and fabrics and, more particularly, but not exclusively, to methods of generating and using same in various therapeutic applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have uncovered a unique method of generating fibers from a natural protein such as a globular protein, and provide, for the first time, a fiber made essentially of albumin.

Figure 19:
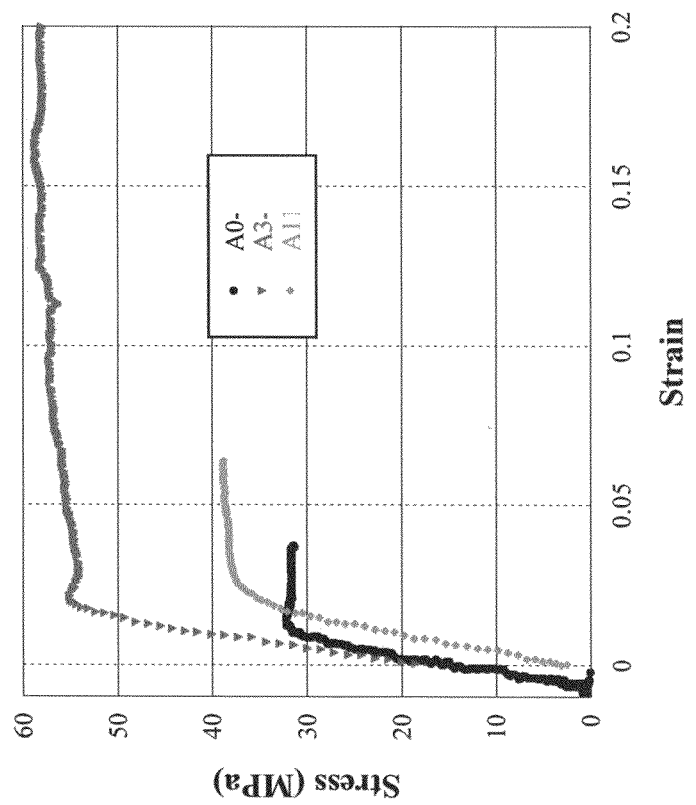
Figure 20:
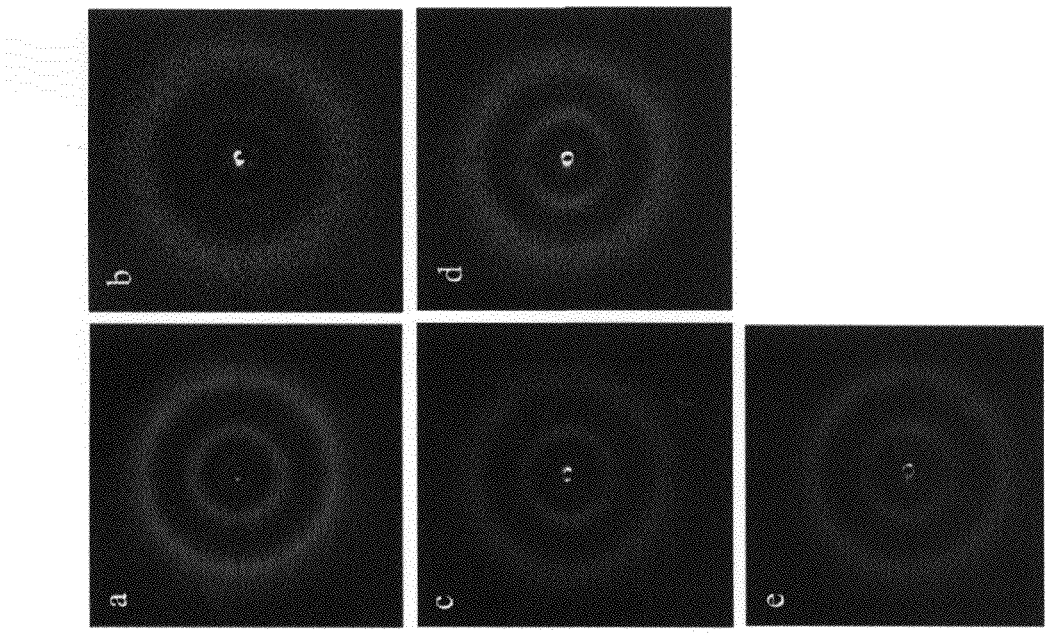
Figure 21:
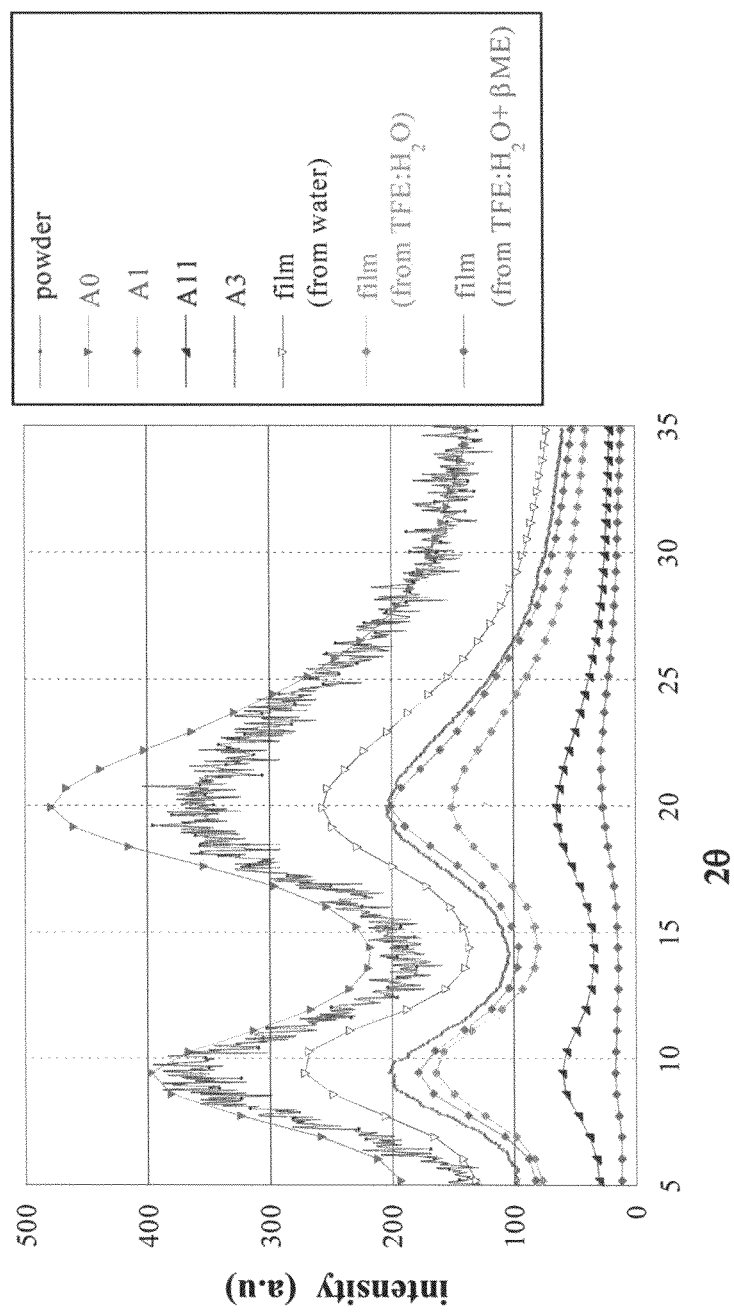

Following is a brief summary of the Examples section illustrating particular embodiments of the invention. In one example (Example 1 of the Examples section which follows) fibers are formed by electrospinning of a solution of albumin in Trifluoroethanol (TFE) and water. The addition of a plasticizing agent such as glycerol to the solution resulted in resilient fibers of 5-10 mm long, with diameters ranging from 500-900 nm. In another example (Table 1, Example 3 of the Examples section which follows) albumin fibers generated by electrospinning exhibited excellent mechanical properties with an elastic modulus in the range of about 45-215 MPa and a tensile strength ($\sigma_{max}$) in the range of about 1-4.6 MPa. In another example (Example 8 of the Examples section which follows), the addition of a reducing agent such as β-mercaptoethanol (β-ME) to the albumin solution containing TFE and water resulted in long albumin fibers (e.g., of 1-20 cm) with diameters ranging from 300-1500 nm (FIG. 18). In another example (FIGS. 19a-c; Example 8 of the Examples section which follows), albumin fibers formed from a solution containing a reducing agent (β-ME) exhibit superior mechanical properties with an elastic modulus in the range of about 1400-2500 MPa and a tensile strength in the range of 30-50 MPa. In another example (Examples 2 and 4 of the Examples section which follows), fabrics made of the albumin fibers were capable of supporting growth of a cell-of-interest [e.g., fibroblast or chondrocyte cells (FIG. 7)], undergo biodegradation by cultured fibroblasts and diminish adherence of S. aureus bacterial cells (FIG. 12) compared with electrospun synthetic PLGA and PCL fabrics, characteristics which are suitable for wound healing. In another example, in vivo experiments demonstrated enhanced wound healing using sutured or light (e.g., laser or a strong source of light) soldered albumin fabrics (FIGS. 14a-b; Examples 2 and 5 of the Examples section), and accelerated re-epithelialization and increased concentration of mast cells in wounds of diabetic experimental animals treated with laser soldered albumin fabrics (FIGS. 15a-d; Example 6 of the Examples section which follows). In another example (FIGS. 16a-c and 17; Example 7 of the Examples section which follows), the albumin fabic could be glued to porcine fascia strips in the presence of a cross linker as glutaraldehyde.

According to one aspect of the invention there is provided a method generating a fiber from a protein. The method is effected by (a) dissolving the protein into a solution, the solution comprises a modifying agent; and (b) evaporating the solution under conditions suitable for formation of the fiber from the protein, thereby generating the fiber from the protein.

As used herein the term "fiber" refers to a man-made elongated filament of a natural protein.

Figure 13:
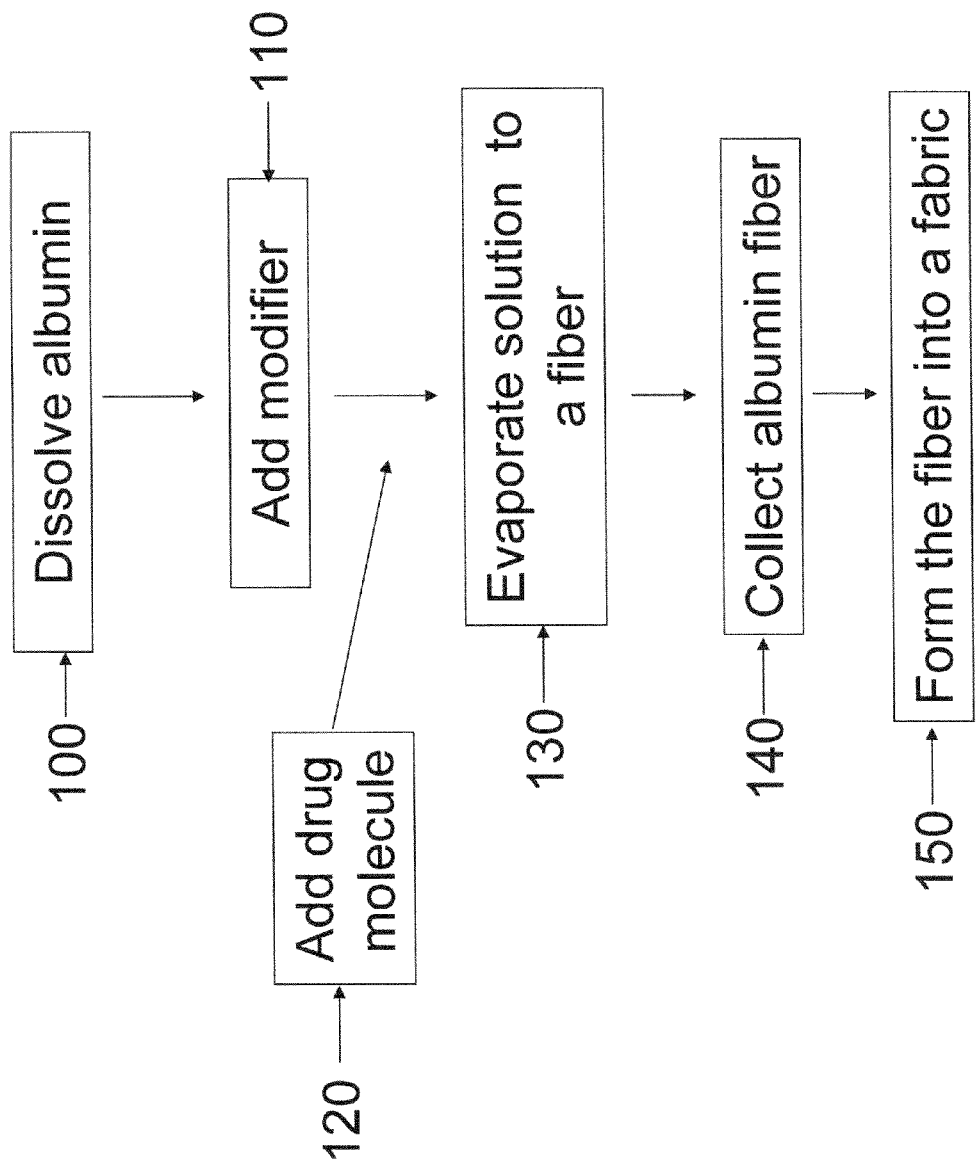

The method according to some embodiments of the invention is schematically depicted in FIG. 13. Referring now to FIG. 13. First the protein is dissolve (e.g., albumin) in a solution (100). Second, a modifier is added (110).

According to one embodiment of the invention, the protein is first dissolved into a solution (an aqueous solution) which comprises a modifying agent. Dissolving the protein can be performed by mixing the protein in the solution (e.g., at room temperature). The solution which includes the dissolved protein therein is further referred to as a "fiber-forming solution" hereinafter.

The concentration of the protein in the fiber-forming solution may be from about 7% to about 20% (w/w), such as from about 9% to about 15%, e.g., from about 9% to about 12%.

The modifying agent can be any element or compound assisting in the process of forming a fiber from the protein.

For example, the modifying agent can be a plasticizing agent, a reducing agent, a denaturing agent or a pH modifying molecule.

As used herein a "plasticizing agent" refers to a compound, which increases flexibility, reduces stiffness and/or controls viscosity (e.g., lowers viscosity to prevent coagulation) of the fiber of some embodiments of the invention. Typical plasticizers are low molecular weight organic or inorganic molecules (e.g., low molecular weight polymers). Examples of organic plasticizers include, but are not limited to, glycerine, ethylene glycol, polyethylene glycol, 1,2-propane diol, 1,3-propane diol, 1,3 butane diol, 1,4 butane diol, pentaerythritol, glucose, starch and a combination thereof. A non-limiting examples of an inorganic plasticizer is sulfur. The plasticizing agent used according to some embodiments of the invention can be biocompatible and/or biodegradable.

According to an embodiment of the invention the plasticizing agent is glycerine (glycerol).

The concentration of glycerol in the fiber-forming solution can be from about 1% to about 30%, such as from about 15% to about 30%, e.g., about 15%, about 20%, about 25%, about 30% glycerol. The glycerol included in the fiber-forming solution may not form part of the force carrying structure of the fiber, or at least be less than 30%, less than 20%, less than 15%, less than 10% of the force carrying structure.

As used herein the phrase "denaturing agent" refers to a compound capable of altering the natural state (e.g., the conformation of the three-dimensional structure) of a native protein by interfering with the non-covalent bonds (e.g., hydrogen bonds or Van de Waals bonds) between the amino acids of the protein.

According to some embodiments of the invention, the concentration of the denaturing agent in the fiber-forming solution, and/or the ratio between the denaturing agent and the water in the fiber-forming solution, and/or the ratio between the denaturing agent, water and protein within the fiber-forming solution are selected such that they enable disruption of the protein tertiary structure while preserving the protein secondary structure (e.g., the a-helix structure). Any of these parameters may vary depending on the specific tertiary structure of each protein.

The denaturing agent can be an alcohol such as methanol ($CH_3OH$) or ethanol ($CH_3CH_2OH$), or it can be a fluorinated alcohol such as 3,3,3,3',3',3'-hexafluoro-2-propanol [HFIP; $(CF_3)_2CHOH$] or 2,2,2-Trifluoroethanol (TFE; $CF_3CH_2OH$) (T. Banerjee, N. Kishore, 2005; Biopolymers, 78:78-86).

According to some embodiments of the invention, the denaturing agent is Trifluroethanol (TFE).

For example, in order to interfere with the tertiary structure of albumin while preserving the albumin α-helix (secondary structure), the concentration of TFE in the solution used to dissolve the protein (the solvent of the fiber forming solution) can be from about 80%-99% (w/w), e.g., from about 82%-97%, e.g., from about 85%-95%, e.g., from about 85-90%, e.g., 90% (w/w) (in water). TFE can be added to the solution at various temperatures such as from about 15° C.-30° C., e.g., about 18° C.-25° C., about 18° C.-23° C.

As used herein the phrase "reducing agent" refers to an element or a compound which is an electron donor in a redox (reduction-oxidation) reaction.

Non-limiting examples of reducing agents which can be used along with the invention include 2-Mercaptoethylamine.HCl, Cysteine.HCl, Thiosulfate, glutathione, homocysteine and β-mercaptoethanol (β-ME).

For example, a reducing agent can break disulfide (S—S) bonds in a protein.

According to an embodiment of the invention, the concentration of the reducing agent in the fiber-forming solution of this aspect of the invention is selected such that it enables denaturation of S—S bonds forming the tertiary structure of the protein while preventing disruption of the protein secondary structure (e.g., α-helix in the case of albumin; see Example 8 in the Examples section which follows).

The concentration of β-ME in the fiber-forming solution is dependent on the tertiary structure of the protein forming the fiber. For example, as shown in Table 3 (Example 8 of the Examples section which follows), β-ME can be added at a concentration which is in proportion to the di-sulfide bonds of the protein. According to some embodiments of the invention, 2-30 molecules (equivalents) of β-ME are added to each di-sulfide bond in the protein, e.g., 8-12 equivalents of β-ME are added to each di-sulfide bond in the protein, e.g., 10 molecules (equivalents) of β-ME are added to each di-sulfide bond in the protein. The number of di-sulfide bonds in the protein can be determined using proteomic analyses. The concentration of β-ME can control the level of opening (break) of S—S bonds within the protein and accordingly the degree of inter-molecular S—S bonds formed within the polymer.

According to some embodiments of the invention, the concentration of β-ME in the solvent of the fiber-forming solution of this aspect of the invention can be in the range of about 0.5-3 (w/w) in water, e.g., about 0.5%.

It was found that when using a reducing agent such as β-ME in the fiber-forming solution (which is optionally devoid of glycerol), the intra S—S bonding within the protein are broken. In an exemplary embodiment of the invention, the formation of new intra and inter molecular S—S bonds during the evaporation process (of the solution) is enhanced by performing the evaporation in the presence of an oxidizing agent such as oxygen.

In an exemplary embodiment of the invention (Table 3 and Example 8 of the Examples section which follows), the presence of a basic solution (high pH) increases tensile stress of the fiber (FIGS. 19b and c) and enhances elastic modulus of the fiber (FIG. 19a). The high pH (basic environment) may be favorable for the reducing agent (β-ME) to reduce the protein S—S bonds.

According to some embodiments of the invention, the fiber-forming solution of this aspect of the invention (which is optionally devoid of glycerol) comprises a high pH, such as a pH which is higher than 7.5, e.g., higher than 8, higher than 8.5, e.g., about 9-10.

In an exemplary embodiment of the invention (Table 3 and Example 8 of the Examples section which follows), the presence of an acidic solution (low pH), increases the tensile stress of the fiber (FIGS. 19b and c) and enhances elastic modulus of the fiber (FIG. 19a). The low pH may help in unfolding the globular structure. For example, at acidic conditions, albumin becomes pronouncedly expanded, a conformation termed as E form and the aggregation of the molecules is inhibited since the protein is highly positively charged. Under these conditions, the solution consists of opened, elongated and isolated chains, a situation which is most favorable for the spinning process and the stretching of the molecules during the process.

According to some embodiments of the invention the modifying agent is a pH-modifying molecule which affects the pH of the fiber-forming solution. Such a molecule can be any strong acid (e.g., HCl) or strong basis (e.g., NaOH) which can added to the solution to achieve a certain pH.

According to some embodiments of the invention, at an acidic fiber-forming solution (e.g., pH 2), even without a reducing agent (or at very low concentrations thereof, e.g., about 1-10%) the protein can be in a more open configuration which is favorable for formation of a protein polymer and fiber formation.

According to some embodiments of the invention the solvent of the fiber-forming solution may include a denaturing agent (e.g., TFE) and may have low pH (e.g., less than 6.5, e.g., pH of 2-3).

According to some embodiments of the invention, the fiber-forming solution of this aspect of the invention (which is optionally devoid of glycerol) comprises a low pH, such as a pH which is lower than 6.5, e.g., lower than 5, e.g., lower than 4, e.g., lower than 3, e.g., about 2.

According to some embodiments of the invention, the combination of a denaturing agent, a basic or acidic solution (low or high pH) and/or a reducing agent may affect the protein tertiary structure such that it is suitable for fiber forming. Any of these parameters may vary depending on the specific tertiary structure of each protein.

According to some embodiments of the invention, the properties of the protein fiber (e.g., adhesiveness, rigidity, tensile, strength, elastic modulus, toughness) can be selected according to the intended use and the fiber can be produced according to the desired properties by applying modifying agents as described (e.g., denaturing agent, reducing agent, pH, plasticizer) at a concentration (of pH value) which is capable of forming a fiber with the desired properties.

For therapeutic applications, the components of the protein fiber (e.g., albumin and plasticizing agent) are preferably sterile (i.e., free of living organisms such as bacteria and yeast) and are of high purity, more preferably medical grade purity (i.e., safe for administration) and even more preferably implant grade purity (i.e., safe for implantation).

Referring now to FIG. 13. Once the protein is dissolved in the solution, the solvent of the protein may be evaporated for fiber formation (130).

According to some embodiments of the invention, the evaporation process is performed under conditions which prevent damage to the protein and yet enable fiber formation. Such conditions may include presence of oxygen (e.g., atmospheric pressure and air). The temperature is selected such that it does not cause uncontrolled denaturation and yet enables fiber formation. Such a temperature can be between about 15° C. to 30° C., e.g., at room temperature (e.g., about 18° C.-20° C.).

According to some embodiments of the invention, forming the fiber is effected by extruding the solution in an electric field.

Extrusion of the solution can be performed by placing the solution in a dispenser forming the spinneret within an electrostatic field in a direction of a collector. The dispenser can be a capillary dispenser such as a syringe with a metal needle or a bath provided with one or more capillary apertures from which the solution can be extruded, e.g., under the action of hydrostatic pressure, mechanical pressure, air pressure and high voltage.

The collector serves for collecting the protein fiber thereupon. Such a collector can be a rotating collector or a static (non rotating) collector. When a rotating collector is used, such a collector may have a cylindrical shape (e.g., a drum), however, it will be appreciated that the rotating collector can be also of a planar geometry (e.g., an horizontal disk). The spinneret is typically connected to a source of high voltage, preferably of positive polarity, while the collector is grounded, thus forming an electrostatic field between the dispensing capillary (dispenser) and the collector. Alternatively, the spinneret can be grounded while the collector is connected to a source of high voltage, preferably with negative polarity. As will be appreciated by one ordinarily skilled in the art, any of the above configurations establishes motion of positively charged jet from the spinneret to the collector. Reverse polarity for establishing motions of a negatively charged jet from the spinneret to the collector are also contemplated.

In an exemplary embodiment of the invention, at a critical voltage, the charge repulsion begins to overcome the surface tension of the liquid drop. The charged jets depart from the spinneret and travels within the electrostatic field towards the collector. Moving with high velocity in the inter-electrode space, the jet stretches and solvent therein evaporates, thus forming fibers which are collected on the collector.

During this process the fiber-forming solution evaporates and protein fibers are formed.

In a substantial absence of additional molecules (e.g., a plasticizing agent such as glycerol) and in the presence of the reducing agent (e.g., β-ME) which breaks S—S bonds within the protein, the formed protein fiber comprises a polymer of the protein molecules (e.g., a polymer of albumin).

As used herein the phrase "polymer of the protein molecules" refers to a plurality of units which are connected to each other by at least one inter-molecular bond (protein-protein bond).

According to some embodiments of the invention each unit comprises a protein molecule or a portion of a protein molecule derived from the same protein.

According to some embodiments of the invention, the polymer includes at least 10 units, e.g., at least 50, e.g., at least 100 units.

According to some embodiments of the invention, the inter-molecular bonds may be covalent bonds formed by S—S bonds. According to some embodiments of the invention, the inter-molecular bonds may be other covalent bonds.

The degree of inter- or intra molecular bonds may be controlled by adjusting the pH of the fiber-forming solution and/or the relative concentration of the reducing agent with respect to the solvent (e.g., water, denaturing agent) and the protein molecules. The polymer may include some degree of "open" bonds (e.g., functional SH groups) which may form bonds with active molecules on nearby material (e.g., for adhesiveness purposes ex vivo and in vivo).

According to some embodiments of the invention, substantially all molecules of the protein (e.g., albumin) consisting the polymer (the polymer units) are covalently attached to other protein (e.g., albumin) molecules of the protein polymer.

According to some embodiments of the invention, at least 85% of the protein molecules are covalently attached to other protein molecules, e.g., at least 90%, e.g., at least 95%, e.g., at least 98%, e.g., 99%, e.g., 100% of the protein molecules are attached to other protein molecules of the protein polymer.

For example, each protein molecule can be covalently attached to one protein molecule of the protein polymer forming the same protein fiber and/or to a protein molecule forming another fiber (from the same fiber-forming solution, a nearby fiber) formed during electrospinning. For example, each protein molecule may be attached to at least 2 molecules of the protein polymer, e.g., to 1-20 molecules of the protein polymer, e.g., to 1-10 molecules of the protein polymer, to 1-8 molecules of the protein polymer, to 1-5 molecules of the protein polymer, to 1-3 molecules of the protein polymer. For example, each molecule of the protein polymer is covalently bound to at least one molecule of the protein polymer.

Covalent attachment between protein molecules can be via S—S bonds.

Covalent binding between molecules of the protein polymer may also occur in fibers comprising co-polymers with other protein molecules or other natural or synthetic polymers, as well as in the presence of low concentrations of other agents such as a plasticizing agent.

According to some embodiments of the invention, the protein fiber of the invention comprises at least 70% purity of the protein polymer, e.g., at least 75% purity, at least 80% purity, at least 85% purity, at least 90% purity, at least 95% purity, at least 99% purity, e.g., 100% purity of the protein polymer.

The purity of the protein polymer may be determined by known means.

The purity of the protein fiber may affect its mechanical properties. For example, according to some embodiments of the invention, protein fibers made of albumin and β-ME (Example 8 of the Examples section which follows), exhibited excellent mechanical properties.

The fiber may be formed from a protein having at least 2 functional groups capable of forming a disulfide bond (e.g., SH groups) with another protein molecule (e.g., inter molecular S—S bonds). According to some embodiments of the invention, the functional groups of the protein are unavailable for formation of a disulfide bond with another protein molecule when in the natural state of the protein, e.g., at physiological conditions, of a PH in the range of 7-85, a temperature of 15-37° C. (e.g., 30-37° C.) and physiological salt concentrations (e.g., as in saline). According to some embodiments of the invention, the functional groups of the protein are unavailable for S—S bonding with other protein molecules due to their location within the tertiary structure of the protein (they can be hidden within the structure of the protein) or they may be unavailable since they form intra-molecular S—S bonds (forming the secondary or tertiary structure of the protein).

According to an embodiment of the invention the protein is a globular protein.

As used herein the phrase "globular protein" refers to a protein having a spherical shape (globelike shape) which can be solubilized in an aqueous solution.

Non-limiting examples of globular proteins which can be used by the method of this aspect of the invention include albumin, hemoglobin, fibrinogen, globulins (e.g., α1, α2, β and γ), globin and myoglobin.

According to an embodiment of the invention, the protein is albumin. As used herein "albumin" refers to a 60 kDa water soluble serum protein (e.g., bovine serum albumin). Albumin is characterized by adhesive and homeostatic properties capable of maintaining the osmotic pressure of the blood compartment, it is a carrier for molecules of low water solubility, including lipid soluble hormones, bile salts, bilirubin, free fatty acids (apoprotein), calcium, iron (transferrin), and some drugs and antithrombotic agent and serve as a source for amino acids. Commercially available bovine serum albumin can be purchased as a powder from ICN (Shelton Conn. USA, Cat. No. 160069).

Non-limiting examples of albumin molecules which can be used for generating the albumin fiber of the invention include human albumin (GenBank Accession No. NP_000468.1; SEQ ID NO:1), mouse albumin (GenBank Accession No. NP_033784.1; SEQ ID NO:2), xenopus albumin (GenBank Accession No. NP_001081244; SEQ ID NO:9), dog albumin (GenBank Accession No. XP_855557.1; SEQ ID NO:3), chicken albumin (GenBank Accession No. NP_990592.1; SEQ ID NO:4), monkey albumin (GenBank Accession No. XP_001103956.1; SEQ ID NO:5), bovine albumin (GenBank Accession No. NP_851335.1; SEQ ID NO:6), rat albumin (GenBank Accession No. NP_599153.1; SEQ ID NO:7), cat albumin (GenBank Accession No. NP_001009961.1; SEQ ID NO:8), plant albumin. The albumin fiber may be formed from a combination of one or two proteins (e.g., albumin and fibrin).

Referring no to FIG. 13. Any of the fiber-forming solutions described hereinabove can include at least one additional moiety which upon fiber formation is attached to the fiber (120). In addition, some moieties may be generated during the process of fiber formation, or added afterward to the formed fiber (or fabric).

As used herein the phrase "attached to the fiber" refers to the binding of the moiety to the fiber via covalent or non-covalent binding (e.g., via an electrostatic bond, a hydrogen bond, a van-Der Waals interaction) so as to obtain an absorbed, embedded or immobilized moiety to the fiber of the invention.

Such a moiety can be any naturally occurring or synthetic molecule such as a peptide, a polynucleotide, a carbohydrate or a polysaccharide, a lipid, a drug molecule, a small molecule (e.g., a nucleotide base, an amino acid, a nucleotide, an antibiotic, a vitamin or a molecule which is smaller than 0.15 kDa), or any combination thereof.

The drug molecule may be any synthetic, chemical or biological molecule. Non-limiting examples of biological drug molecules include antisense oligonucleotides, Ribozymes, DNAzymes, siRNA, receptor agonists, antagonists, hormones, growth factors and antibodies. Non-limiting examples of which chemical drug molecules include chemotherapy agents, antiinflammatory drugs, Paclitaxel (Taxol®), radiation seed particles (e.g., see Hypertext Transfer Protocol://World Wide Web (dot) oncura (dot) com), as well as natural or synthetic vitamins.

The fiber may also be attached to a cell-of-interest (a prokaryotic or eukaryotic cell) such as a stem cell (examples are provided hereinbelow).

Under certain conditions the attached moiety or cell can be released from the fiber (e.g., by immersing the fiber in an aqueous solution which enhances the desorption of the moiety/cell from the fiber) be used for various ex vivo or in vivo applications (e.g., drug release).

The fiber-forming solution may further include a dye (light absorbing agent). The dye may selectively absorb light so that the absorbed light energy heats the near environment (e.g., the fiber or adjacent material). The heat may be used to assist in attachment of the fiber to a nearby tissue or fiber. Non-limiting examples of dyes which can be used include Indocyanine green (ICG), methylene blue, India ink, rose bengal, fluorescein isothiocyanate (FITC), acridine orange, food coloring and the like.

The teachings of various embodiments of the invention (using any of the above-described methods) were used to generate, for the first time, a fiber consisting essentially of albumin (an albumin fiber).

As used herein the phrase "consisting essentially of" refers to the presence of albumin as the structural unit of the fiber.

According to an embodiment of the invention, the albumin fiber of the invention includes at least 50%, at least 55%, at least 60%, at least 65%, at least 70%, at least 75%, at least 80%, at least 85%, at least 90%, at least 95%, at least 96%, at least 97%, at least 98%, at least 99%, e.g., 100% albumin (% in weight/weight).

The albumin molecules in the fiber comprise the structural strength of the fiber. As used herein the phrase "structural strength" refers to the fiber mechanical properties such as elastic modulus, tensile stress, elongation (strain) and toughness [combination of tensile stress and elongation (strain)].

According to some embodiments of the invention, more than about 50% of the structural strength of the fiber results from albumin, e.g., more than about 60% of the structural strength of the fiber results from albumin, e.g., more than about 70% of the structural strength of the fiber results from albumin, e.g., more than about 80%, more than about 90%, e.g., about 95%, about 99%, e.g., 100% of the structural strength of the fiber results from albumin.

According to some embodiments of the invention, the albumin fiber may also include additional polymers or proteins.

According to an embodiment of the invention, the albumin fiber which is made using a reducer agent (β-ME) is characterized by an elastic modulus of at least 1000 MPa, e.g., at least 1500 MPa. According to some embodiments, such an albumin fiber is characterized by an elastic modulus in the range of about 1400 MPa to about 2500 MPa, e.g., in the range of about 1500-2500 Mpa.

According to an embodiment of the invention, the albumin fiber which is made using a reducer agent (β-ME) is characterized by a peak stress [tensile strength ($\sigma_{max}$)] of at least 20 MPa, e.g., at least 30 MPa. According to some embodiments, such an albumin fiber is characterized by a peak stress [tensile strength ($\alpha_{max}$)] in the range of about 15-65 MPa, e.g., 30-50 MPa.

According to an embodiment of the invention, the albumin fiber of the invention is modulated by glycerol.

As used herein the phrase "modulated by glycerol" refers to a fiber formed from a solution containing glycerol.

According to an embodiment of the invention, the albumin fiber which is made with a plasticizing agent (glycerol), is characterized by an elastic modulus in the range of about 45-215 MPa.

According to an embodiment of the invention, the albumin fiber which is made with a plasticizing agent (glycerol), is characterized by a peak stress [tensile strength ($\sigma_{max}$)] in the range of about 1-4.6 MPa.

The length of the albumin fibers of the invention may vary from a few millimeters to several centimeters (e.g., 1-20 cm).

According to an embodiment of the invention, the fiber which is made with a reducing agent (β-ME) has a length from the range of about 1-20 cm and a diameter from about 300-1500 nm.

According to an embodiment of the invention, the fiber which is made with a plasticizing agent (glycerol) has a length from the range of about 1-10 cm and a diameter from the range of about 500-900 nm.

Referring now to FIG. 13, forming a fabric (150). Long fibers may be collected for knitting, wafting, or other woven or non-woven uses. As mentioned hereinabove and further described in the Examples section which follows, the albumin fibers generated according to some embodiments of the invention were used to generate an albumin fabric.

As used herein the term "fabric" refers to a woven or non-woven artifact made of the protein fiber of the invention. Optionally, the fabric is made with a controlled shape, dimension, porosity and/or pore size.

The shape of the fabric (e.g., a flat circle or tubular structure, top hat shape, spindle shape) depends, for example, on the geometry of the rotating collector on which the fabric is formed. For example, when the collector is a rotating collector such as a drum, the formed fabric may have a disc shape with a radius that is determined by the radius of the drum. Alternatively, when the collector has a tubular structure, the formed fabric is a tubular fabric having an internal the radius of the tubular collector. The shape of the fabric can also depend on the position of the dispenser relative to the collector. For example, the dispenser can rotate while the collector may or may not rotate. Similarly, the length of the tubular fabric is determined by the length of the tubular collector. It will be appreciated that various geometries and dimensions can be used to design the rotating collector, essentially as described in the art (Teo, W. E., Ramakrishna, S., "review on electrospinning design and nanofibre assemblies", NANOTECHNOLOGY 17 (14): R89-R106 Jul. 28, 2006).

The fabric may be molded using heat and solder to another fabric and/or to a stitch or other elements, like a metal framework, or a layer of another fabric or element, depending on its intended use.

As mentioned, the fabric may be formed of weaved or knotted fiber, such as a fiber collected on a cone, which is further weaved or knotted into a product.

The fabric may have preferential fiber direction according to expected direction of forces and/or flexibility. This may be achieved by moving the collecting plate at various speeds.

The thickness of the fabric is determined by the collecting time and flow rate. For example, when the fiber-forming solution is dispensed for 1 hour at a rate of 1 ml/hour towards a drum having a radius of 7 cm, the collected fabric is a circular disc having a thickness of 150 µm and a radius of 7 cm. Alternatively, when the fiber-forming solution is dispensed for 1 hour at a rate of 1 ml/hour and collected on a tubular collector with a radius of 7 cm and a length of 2-10 cm, the collected fabric is a tube having a thickness of 120 µm, a radius of 7 cm and a length of 2-10 cm.

A fabric can be of various dimensions such as a radius from 5-10 mm, a thickness from 0.1-4 mm and/or a tubular length from 5-150 mm. In addition, the porosity and/or the pore size of the fabric can be controlled by modulating the electrostatic field. The porosity may be about 70-95%, about 87-93%, and the average pore size of the fabric can be from about 1 to about 50 µm in diameter.

In an exemplary embodiment of the invention the fabric can be formed from one type of fibers or from several types of fibers. For example, the fabric can include fibers made of different proteins (e.g., albumin fibers and fibrin fibers), or fibers which include different moieties attached thereto [e.g., one type of fibers includes an anticoagulation drug attached thereto and another type of fibers includes a growth factor (e.g., VEGF) attached thereto].

The fabric formed from the protein fiber may be subject to post processing which may adjust the fabric according to specific uses. For example, the fabric can be subject to thermal curing.

As used herein "curing" is the process by which the physical properties of a material are changed into a more stable and/or usable condition. This is accomplished, for example, by the use of heat (i.e., thermal curing), radiation or reaction with chemical additives.

According to an embodiment of the invention, thermal curing is effected at a temperature range of about 60-95° C., such as at a temperature range of about 70-90° C., about 85-90° C., e.g., about 85° C.; at humidity conditions of 30-100%, e.g., 80-95%; and for a duration of about 10-120 minutes, e.g., for about 30-120 minutes, about 60-120 minutes, e.g., about 60 minutes.

Following curing, the shape of the fabric can be maintained by placing the fabric between plates or molds (e.g., two aluminum plates which keep the fabric's shape straight compared with aluminum foil), by stretching the fabric putting a weight thereon (e.g., an even or non-even weight).

The fabric may be dehydrated so as to minimize the remaining water (trace water) in the fabric (e.g., to less than 5% trace water).

The fabric may be subject to plasma treatment (e.g., etching). Plasma etching (e.g., shot in pulses of a high stream of ionized gas) can be performed by ionized $O_2$ using a PDE 301 planar plasma etcher (LFE Corp., Clinton, Mass.) at 50 W and 10 $cm^3$/min oxygen volumetric flow rate, for a time period from the range of 10-150 seconds, such as for 30", 60" and 120". Additionally or alternatively, Nitrogen oxygen and high-molecular-weight fluorocarbon may be used for plasma treatment.

According to an embodiment of the invention, plasma etching is effected so as to reduce water molecules from the fiber and/or sterilize the fiber/fabric.

Layers of the fabric (e.g., an outer layer or an inner layer) may be coated and collected layer by layer. Adhesion is achieved due to physical interaction between the layers (Van der walls forces).

As mentioned, the fiber used to generate the fabric may include a dye which can be used for laser soldering. For example, in case ICG is used, the fabric can be laser soldered to another fabric or a tissue by employing a laser beam [e.g., of a GaAs laser (Lumenis, Model 6030, Israel); wavelength $\lambda$=810-830 nm], with a beam spot of e.g., 6 mm activated for 10-60 seconds from a distance of about 0.5-10 cm from the fabric.

The fabric of some embodiments of the invention may be attached to another material or a tissue by cross-linking [e.g., with glutaraldehyde; see Example 7 or other known agents such as formaldehyde, Genipin, diepoxide-,4-butanedioldiglycidyl ether (BDDE)]. Cross-linking can be performed using non-toxic concentrations of the cross-linking agent (e.g., about 0.5%-10%, e.g., about 10%), for a limited time period (e.g., the reaction should be completed within two minutes).

Albumin fabrics of some embodiments of the invention are capable of supporting growth of a cell-of-interest, undergo biodegradation by cultured fibroblasts and/or diminish adherence of S. aureus bacterial cells (see Examples 2 and 4 of the Examples section which follows), they can be used in various therapeutic applications such as wound healing.

According to an aspect of some embodiments of the present invention there is provided a method of bonding a damaged tissue of a subject. The method is effected by introducing to the damaged tissue of the subject an albumin fabric, thereby bonding the damaged tissue of the subject.

The term "bonding a tissue" as used herein refers to fusing, closing, adhering and/or ligating the tissue with the albumin fabric of the invention.

As used herein, the term "subject" includes mammals, preferably human beings at any age.

According to an embodiment of the invention, the subject suffers from a damaged (e.g., wounded) tissue such as following a trauma, a burn, a genetic disease (e.g., skin disorder), an infectious disease, a degenerative or vascular disease (e.g., diabetes), cancer (e.g., skin cancer), or following an incision or an excision made using a surgical tool.

As used herein the phrase "introducing to the damaged tissue of the subject an albumin fabric" refers to providing a portion of the albumin fabric of the invention to the damaged tissue of the subject to thereby enhance bonding of the albumin fabric to the damaged tissue of the subject.

The albumin fabric may be cut to portions having dimensions that fit the dimensions of the damaged tissue of the subject. For example, to bond a surgical incision made for a common Caesarean section (e.g., 15-20 cm long), the albumin fabric can be cut into a square having a width of about 1-2 cm, a length of about 15-20 cm and a thickness of about 500 µm.

According to an embodiment of the invention, the method further comprising suturing the albumin fabric to the damaged tissue of the subject. Suturing can be performed using any known suturing apparatus or tool (e.g., a clip). The fabric can be reinforced at suturing location.

According to an embodiment of the invention, the method further comprising laser soldering the albumin fabric to the damaged tissue of the subject.

Laser bonding can be performed on albumin fabric which include a solder enhancing agent as described hereinabove, e.g., Indocyanine green (ICG).

Albumin fabrics containing ICG are introduced to the damaged tissue of the subject and a source of light such as a laser beam of 810-830 nm wavelength or a flash-lamp is directed at the soldering locations in the albumin fabric (e.g., from a distance of about 0.5 cm-10 cm), for a time period of 10 seconds-60 seconds.

The albumin fabric of the invention can be used in the preparation of dressings for wounds. The fabric may include slowly released therapeutics, antibiotics and growth factors such as Transforming Growth Factor 3 (TGF3) which stimulates the formation of a tactile skin lining. In addition, a combination of a "wafer" of an albumin fabric and a 3D sponge can be used to provide hydrocolloid wound dressing for chronic wounds and improved wound sealing, therapeutic slow release and tissue substitute.

The albumin fabric of the invention can be used to prepare a mesh such as a hernia mesh to repair a hernia (e.g., umbilical hernia, inguinal, femoral, incisional, spigelian, epigastric, and obturator) while supporting natural healing of the torn tissue. The mesh can include strips of non-woven fabrics (as spun albumin mats). The albumin fabric forming the mesh may be fabricated with controlled adhesiveness, by controlling the percentages of the plasticizer (e.g., glycerol) and/or the reducing agent (e.g., β-ME).

Figure 16A:
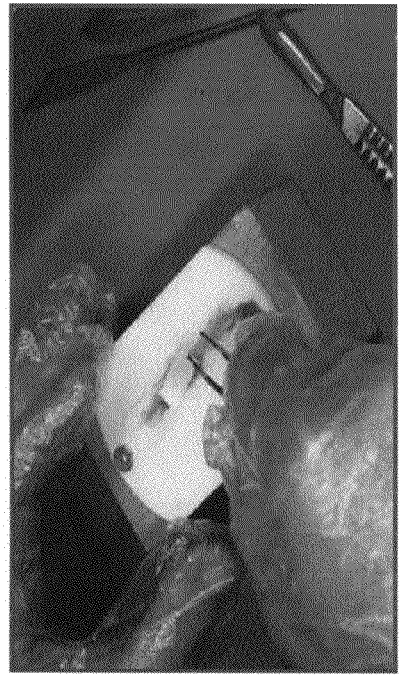
FIGS. 16a-c are photographs depicting the bonding of two porcine fascia strips by placing albumin fabric made of solution D with β-mercaptoethanol and addition of 10% glutaraldehyde over the fascia strips in a wet environment. Bonding was achieved in two minutes and tensile strength was measured using an Instron tensiometer.
Figure 16B:
Figure 16C:
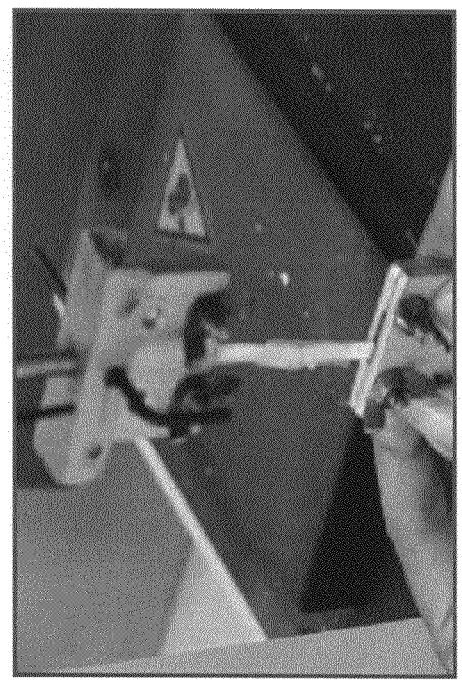
Figure 17:
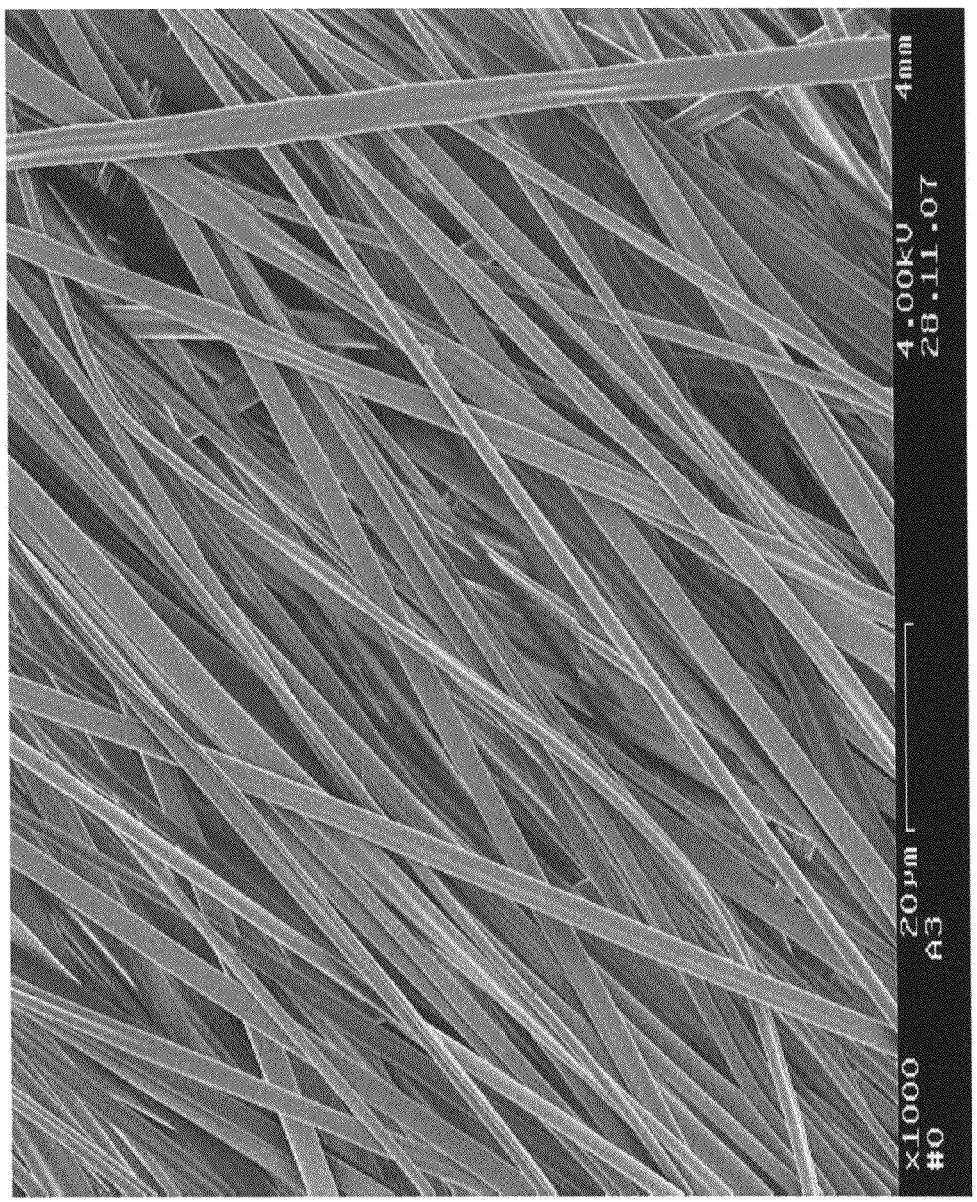

The albumin fabric of some embodiments of the invention can be used as a hemostasis apparatus which is optionally bonded [e.g., using a cross linking agent such as glutaraldehyde (see e.g., Example 7 of the Examples section which follows and FIGS. 16a-c) or a laser bonding] to a heavily bleeding tissue such as torn or damaged tissues of liver or spleen.

In some embodiments, the albumin fabric of the invention can be used as biodegradable tube for sutureless anastomoses, such as sutureless microvascular surgery and to sutureless endoscopic alimentary and urinary tracts bonding.

In some embodiments, the albumin fabric of the invention can be used internally as a supporting stent which is bonded from the outside by a laser or from outside as a sleeve or combination.

In some embodiments, the albumin fabric of the invention can be used as biodegradable "sleeve" for sutureless anastomoses of two segments such as torn tendons or torn nerves. The bioabsorbable albumin sheath-implant provides a non-constricting encasement for injured peripheral nerves or tendon. The wall of the conduit has a longitudinal slit that allows the spread open and easy placement of the sheath for over the injured nerve or tendon. Then the sheath is bonded to the nerves or tendon by employing laser energy or applying a crosslinker such as glutaraldehyde (Example 7). The albumin wrap allows the nerve or tendon to recover and maintain proximity of the two segments.

In some embodiments, the albumin fabric of the invention can be used as biodegradable stent for insertion as glaucoma shunts In some embodiments, the albumin fabric of the invention can be used as an artificial blood vessel to replace blood vessels grafts for Coronary Artery Bypass Graft (CABG) or vascular implants such as for aurthobifemoral bypass.

In some embodiments, the albumin fabric of the invention can be used to seal damaged or torn dura which results in cerebral spinal fluid (CSF) leak. The albumin fabric can be implanted into an open space and further laser-bonded or cross linked (using e.g., glutaraldehyde) to the space margins (similar to connecting a patch).

In some embodiments, the albumin fabric of the invention can be used to coat a stent in order to reduce formation of thrombi and for releasing drugs in case of drug-eluting stents.

In some embodiments, the albumin fabric may be used to filter cells out of suspension (by controlling the pore size in the fabric).

As mentioned the fabric of the invention can be designed with controlled porosity and pore size. It will be appreciated that an albumin fabric with controlled porosity can be used as a scaffold which enable migration and/or proliferation of specific cell types therethrough.

Thus, the albumin fabric of the present invention can be used for ex vivo and/or in vivo formation of a tissue.

The phrase "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Thus, according to an additional aspect of specific embodiments of the invention there is provided a method of inducing ex vivo formation of a tissue. The method is effected by: (i) providing an albumin fabric; and (ii) seeding the albumin fabric with cells in a medium selected suitable for proliferation, differentiation and/or migration of the cells to thereby induce the ex vivo formation of the tissue.

Once seeded on the matrix (the albumin fiber) the cells used by the method of this aspect of the invention are capable of forming a tissue. Such cells can be for example, stem cells such as embryonic stem cells, bone marrow stem cells, cord blood cells, mesenchymal stem cells, adult tissue stem cells, or differentiated cells such as neural cells, retina cells, epidermal cells, hepatocytes, pancreatic cells, osseous cells, cartilaginous cells, elastic cells, fibrous cells, myocytes, myocardial cells, endothelial cells, smooth muscle cells, and hematopoietic cells.

As used herein the phrase "stem cell" refers to cells which are capable of differentiating into other cell types having a particular, specialized function (i.e., "fully differentiated" cells) or remaining in an undifferentiated state hereinafter "pluripotent stem cells".

Non-limiting examples of stem cells are hematopoietic stem cells obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation, and/or adult tissue stem cells [i.e., mesenchymal stem cells (MSCs)].

The term "seeding" refers to plating, placing and/or dropping the cells into the albumin fabric of the invention. The concentration of stem cells which are seeded on or within the albumin fabric of the invention may depend on the type of cells used and the structure of the albumin fabrics of the invention (e.g., porosity and pore size).

The medium used according to this aspect of the present invention can be any tissue culture medium supplemented with minerals and growth factors suitable for inducing the proliferation, differentiation and/or migration of the cells (e.g., stem cells) of the invention into more specialized (i.e., differentiated) cells.

Following seeding the cells in the albumin fabric of the invention the fabric can be routinely examined using a microscope (e.g., an inverted microscope, an axioplan light microscope or an electronic microscope) for evaluation of cell growth, spreading and tissue formation.

Optionally, the ex vivo formed tissue is implanted in a subject in need thereof (e.g., a subject suffering from a pathology requiring tissue regeneration and/or repair). In such cases the cells seeded on the albumin fabric (the scaffold) for ex vivo formation of a tissue can be derived from the treated individual (autologous source) or from allogeneic sources such as embryonic stem cells which are not expected to induce an immunogenic reaction. Those of skills in the art are capable of determining when and how to implant the scaffold to thereby induce tissue regeneration and treat the pathology.

As mentioned, the albumin fabric of the invention can be further used for in vivo formation of a tissue (to induce tissue regeneration and/or repair in a subject).

Thus, according to yet an additional aspect of specific embodiments of the invention, there is provided a method of inducing in vivo formation of a tissue. The method is effected by: (i) providing an albumin fabric; and (ii) implanting the albumin fabric in a subject to thereby induce the in vivo formation of the tissue.

Along with the cells, the fabric may be seeded with a cell migration and/or growth modulator (e.g., growth factors).

According to an embodiment of the invention, the method comprises suturing or laser bonding of the albumin fabric to a tissue of the subject.

Thus, the albumin fabric of the invention which can be used to induce tissue formation and/or regeneration can further treat individuals suffering from a pathology characterized by tissue damage or loss.

As used herein the phrase "pathology characterized by tissue damage or loss" refers to any disorder, disease or condition exhibiting a tissue damage (i.e., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration. Examples for disorders or conditions requiring tissue regeneration include, but are not limited to, liver cirrhosis such as in hepatitis C patients (liver), Type-1 diabetes (pancreas), cystic fibrosis (lung, liver, pancreas), bone cancer (bone), burn and wound repair (skin), age related macular degeneration (retina), myocardial infarction, myocardial repair, CNS lesions (myelin), articular cartilage defects (chondrocytes), bladder degeneration, intestinal degeneration, and the like.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The albumin fiber and/or the albumin fabric of some embodiments of the invention may be included in a kit and/or an article-of-manufacturer. The article-of-manufacturer comprises packaging material and the albumin fiber or fabric of some embodiments of the invention, and is identified in print in or on the packaging material for therapeutic use as described hereinabove.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

An electrospinning apparatus can include a controller programmed with parameters as described herein or measuring output and automatically modifying. Controller can be hardware, software, firmware, with CPU, volatile memory, optional non-volatile memory.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Materials:
Bovine Albumin Fraction V was supplied by MP Biomedicals (Israel).
Trifluroethanol (TFE) was purchased from Aldrich-(U.S.A.).
Glycerol was purchased from Frutarom (Israel).
Indocyanine green (ICG-1 mg/ml, MP Biochemical, Inc) serving as dye-enhanced solder was supplied MP Biochemical (Israel).
All the materials were used without further purification.
Solutions Used for Electrospinning of Albumin:
Solution A: 12% Albumin in TFE.
Solution B: 12% Albumin in TFE/water w/w (9:1).
Solution C: 12% Albumin, 15% Glycerol/Albumin in TFE/water w/w (9:1)
Solution D: 12% Albumin, 30% Glycerol/Albumin in TFE/water w/w (9:1) and 0.5% beta-mercaptoethanol (w/w).
Solution E 10% Albumin TFE:$H_2O$ 9:1+10 eq/bond β-ME
Solution F 10% Albumin TFE: Ammonium hydroxide 0.1 M 9:1+10 eq/bond β-ME pH~9
Solution G 10% Albumin TFE: HCl 0.1M 9:1+10 eq/bond β-ME pH~2

Solution H: 1-50% albumin in water.
Sample Preparation—
The solutions underwent electrospinning from a 5 ml syringe with a hypodermic needle having an inner diameter of 0.5 mm. The flow rate was Q=0.2-0.5 ml/hour. A copper electrode was placed in the polymer solution and the suspension was spun onto the edge of a grounded collector disk (for more details on electrospinning see Theron A., et al., 2001) and on horizontal disk. The strength of the electrostatic field was E=1.1 kV/cm and the distance between the electrode tip and the edge of the disk (or the horizontal disk) was 12 cm. The linear speed at the edge of the disk collector was V=8.8 m/s. All the experiments were performed at room temperature (about 24° C.), and a humidity of about 50%. The samples stored for 24 hours in a desiccator (humidity of about 30%). These parameters could be varied to control the electrospinning process using methods known in the art.

Thermal Curing of Albumin Fabrics—
The electrospun fabric made from solution D was optionally desiccated within a lyophilizer overnight and was placed between two aluminum plates (plates keep the fabric's shape straight compared with aluminum foil situated at the bottom of a 600 ml Beaker glass covered on top with aluminum foil. The 600 ml Beaker glass was placed within a thermostatic water bath (model WB-5, Fried Electric, Haifa Israel) covered with aluminum foil on top and the albumin fabric was thermally cured at 85° C. for 60 minutes.

Characterization of Nanofibers Morphology—
was done using a high-resolution scanning electron microscope (HR-SEM; Leo Gemini) operating at an accelerating voltage of 3 kV and a current of 120 pA.

Characterization of Nanofibers Mechanical Properties—
The mechanical properties of the fibers were studied by the tensile testing (uniaxial stretching) of a ribbon. A ribbon of aligned electrospun nanofibers was detached from the vertical rotating disc. A custom built screw driven testing machine with a 50 gf load-cell was used, under displacement control, with a resolution of 12 mgf, and velocity of 1 mm/second. Since large strain testing by the present set up of a single fiber is below the available resolution of the setup, experimental load was recalculated into tensile stress, with the central assumption that all the aligned fibers experience the same stress level. Consequently, the nominal fiber strain was determined according to equation (1):

$$\varepsilon_f = \Delta L / L_0$$

and fiber stress was determined according to equation (2):

$$\sigma_f = P/A$$

where $\Delta L$ and $L_0$ stand for elongation and initial gauge length, respectively, P is the measured load and A is the average nanofibers' ribbon cross section.

FT-IR measurements of the electrospun fiber as well as the albumin in its native form were analyzed by Bruker's Vector22 FT-IR and Bruker's Equinox55 FTIR.

Example 1

Electrospinning of Albumin Nanofibers and Fabrics

Figure 1B:
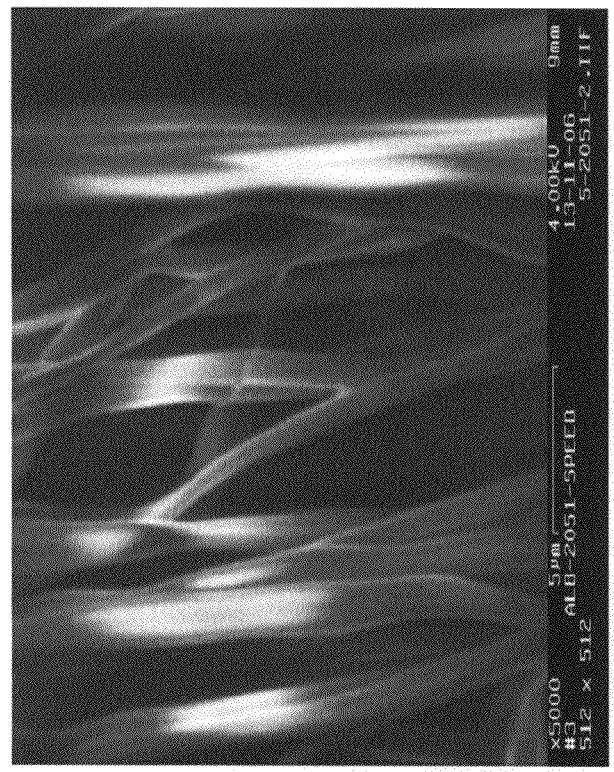
FIGS. 1a-b are images of as-spun fibers (made of solution C)-collected on horizontal electrode (FIG. 1a), and on the edge of a vertical spinning electrode-disc (FIG. 1b).
Figure 1A:
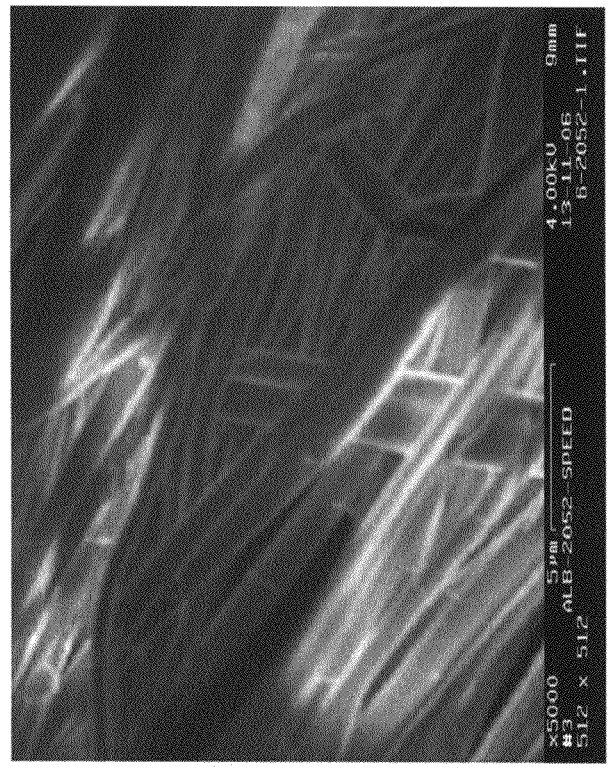

Experimental Results
Generation of Albumin Fibers by Electrospinning—
Electrospinning of albumin at any concentration from 1-50% in water (various concentrations of albumin in solution H) was not spinnable, and could not result with any albumin fiber. Electrospinning of solution A, resulted in short fibers (fragments) with a length of hundreds microns (e.g., 200-5000 μm) and a diameter of about 3 microns. By adding water as co-solvent (Solution B) a continuous electrospinning was obtained, however the resulting fabric was brittle with a typical length of 5000-10000 μm and a diameter of about 2 μm. Addition of Glycerol as plasticizer (Solution C) makes the brittle fibers become resilient with long fibers in the range of 5-10 mm with an average diameter of 700 nm. In addition, glycerol improves the electrospinning process by lowering the solution viscosity, which may assist in preventing coagulation. HR-SEM images of a collected non-woven and aligned nanofibers are shown in FIGS. 1a-b.

Generation of a Tube Made of Albumin Nanofibers—

Figure 2:
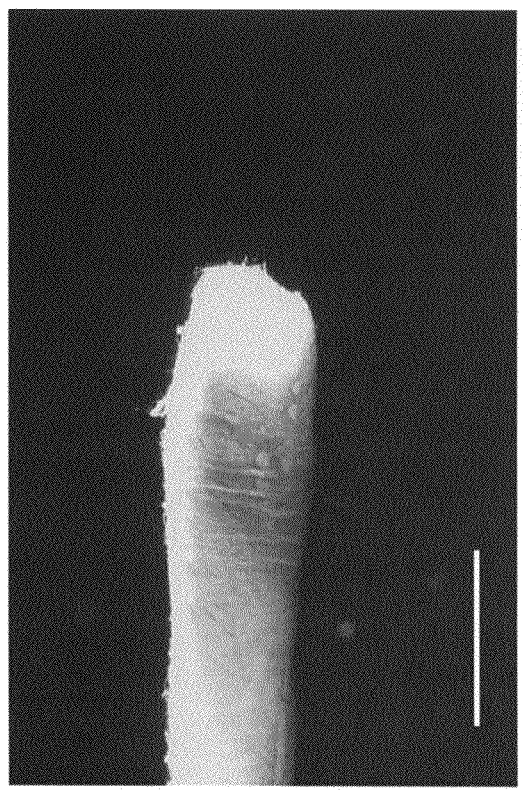
FIG. 2 is an optical image of a tube made of electrospun albumin fibers (Solution C). Size bar—5 mm.

Electrospun nanofibers were also collected around a cylindrical rod forming a tubular structure that depends on the diameter of the collecting rod. An image of tube made of electrospun albumin nanofibers is shown in FIG. 2.

The Secondary Structure of Albumin in the Albumin Fibers—

Figure 3:
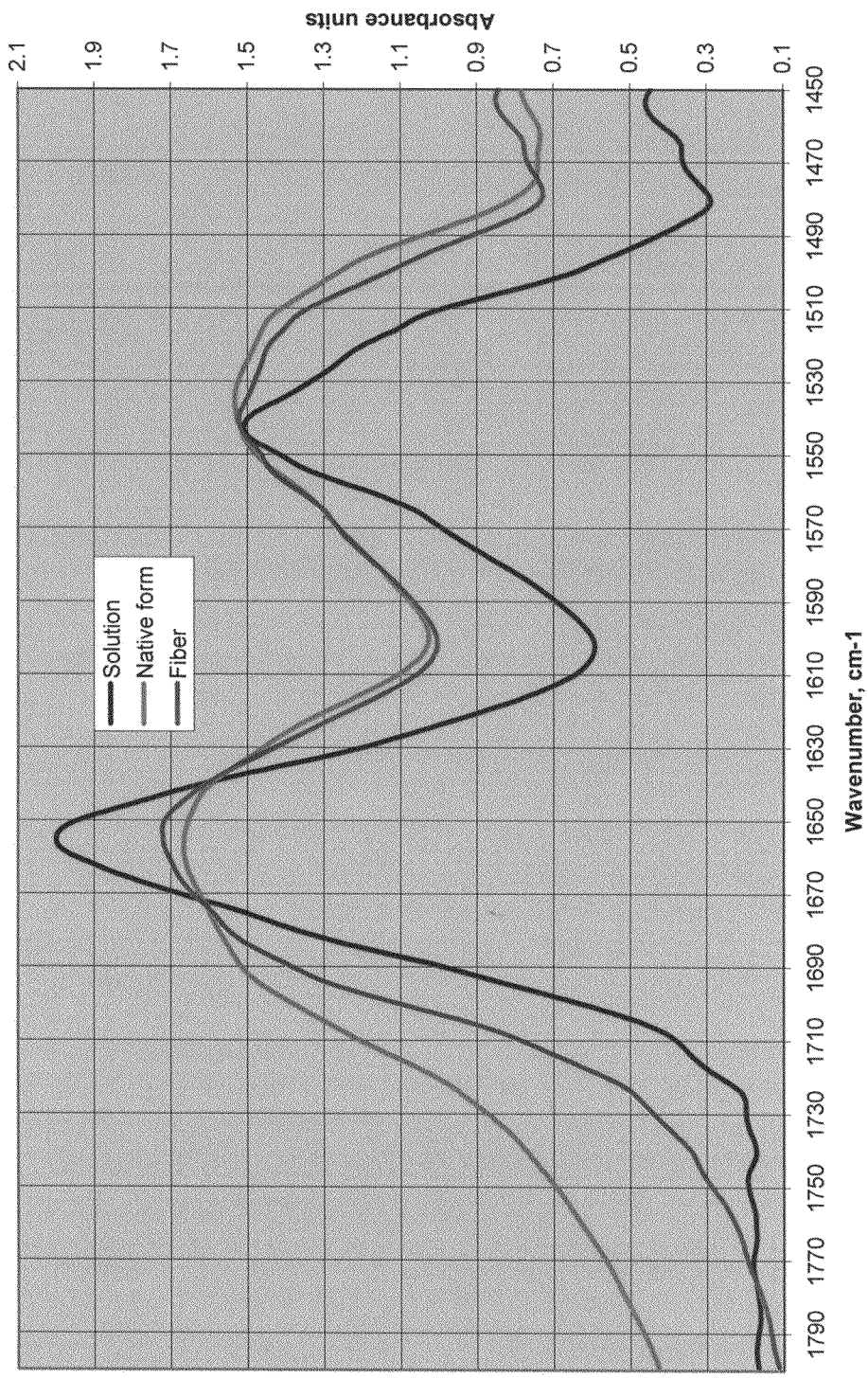
FIG. 3 is a representative FT-IR spectrum of: the albumin native form (pink line), Solution D; blue line], and a ribbon of electrospun fibers originated from Solution C (green line); Y axis: Absorbance units; X axis: Wave number cm$^{-1}$.
Figure 4:
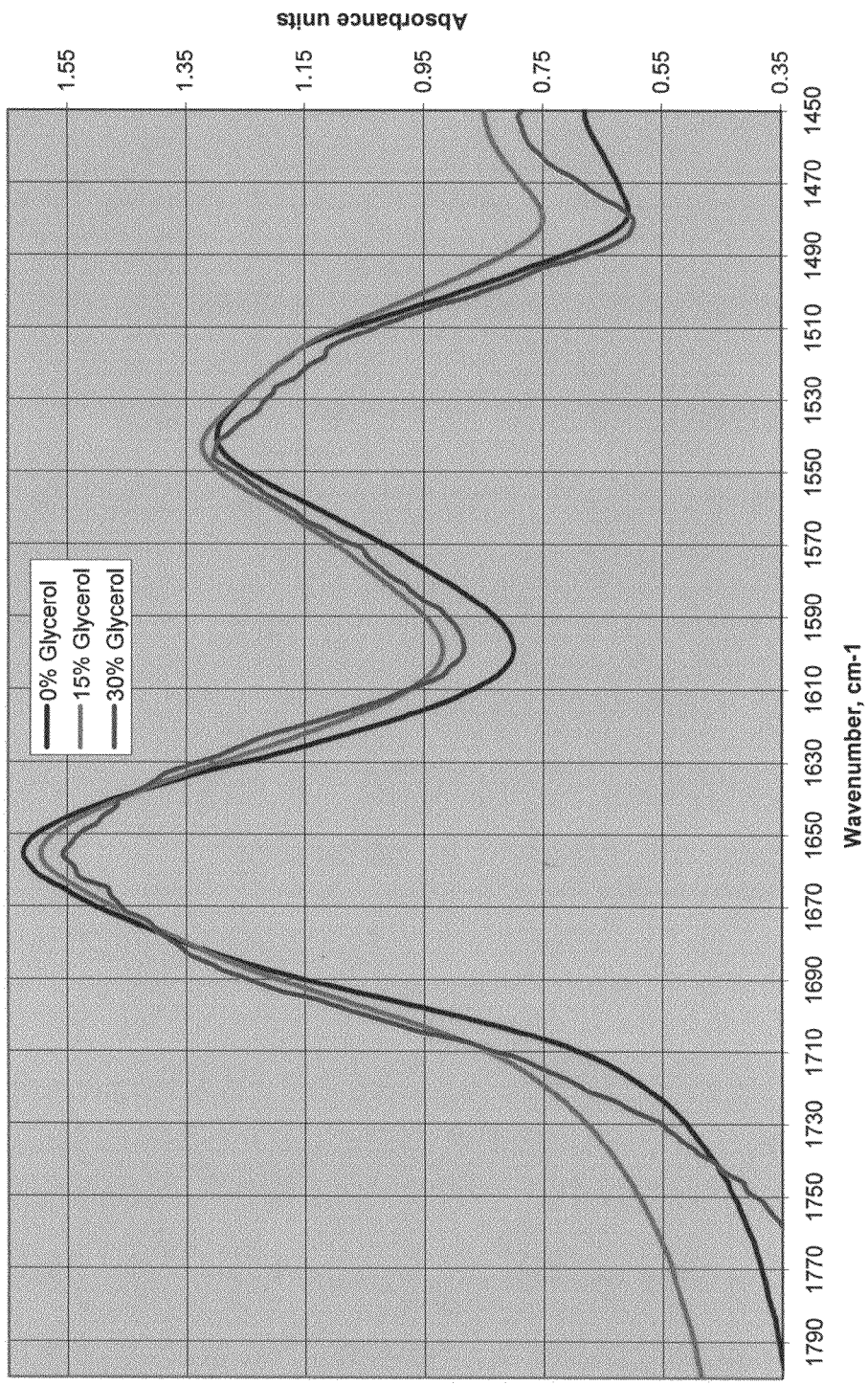
FIG. 4 is a representative FT-IR spectrums of solutions B (12% BSA, TFE:water 9:1, 0% glycerol; blue line), C (12% BSA, TFE:water 9:1, 15% glycerol; pink line) and D (12% BSA, TFE:water 9:1, 30% glycerol; green line); Y axis: Absorbance units; X axis: Wave number cm$^{-1}$.

The secondary structure variation of the native albumin in the solution and electrospun nanofibers was studied using Fourier transform infrared spectroscopy (FTIR). By dissolving the albumin in TFE its globular tertiary structure was affected and more linear molecular structures (α-helix structure) were observed. TFE can support the alpha-helical structures formation by an enforcement of intermolecular hydrogen-bonds. TFE can protect the secondary structure of proteins while decompose the tertiary one. The FTIR spectrum of native BSA, Solution C and as-spun fibers from solution C are shown in FIG. 3. As it clearly shown by spectra comparison, especially in amide-I region, in solution the percent of α-helical structure much higher than in native form or in fiber, the "peak" is sharper and more "Gaussian" like. After fiber formation the "native-like" structure is almost restores, although it does not guarantee that the tertiary structure was recovered. A comparison of the glycerol contribution to the FTIR spectrum is presented in FIG. 4. It can be seen that substantial differences in picture of amide-I and amide-II regions are not observed. This suggests that the differences in fibers properties apparently are not reflected by the secondary structure of the albumin solutions.

Mechanical Properties of Albumin Fabrics—

Figure 5:
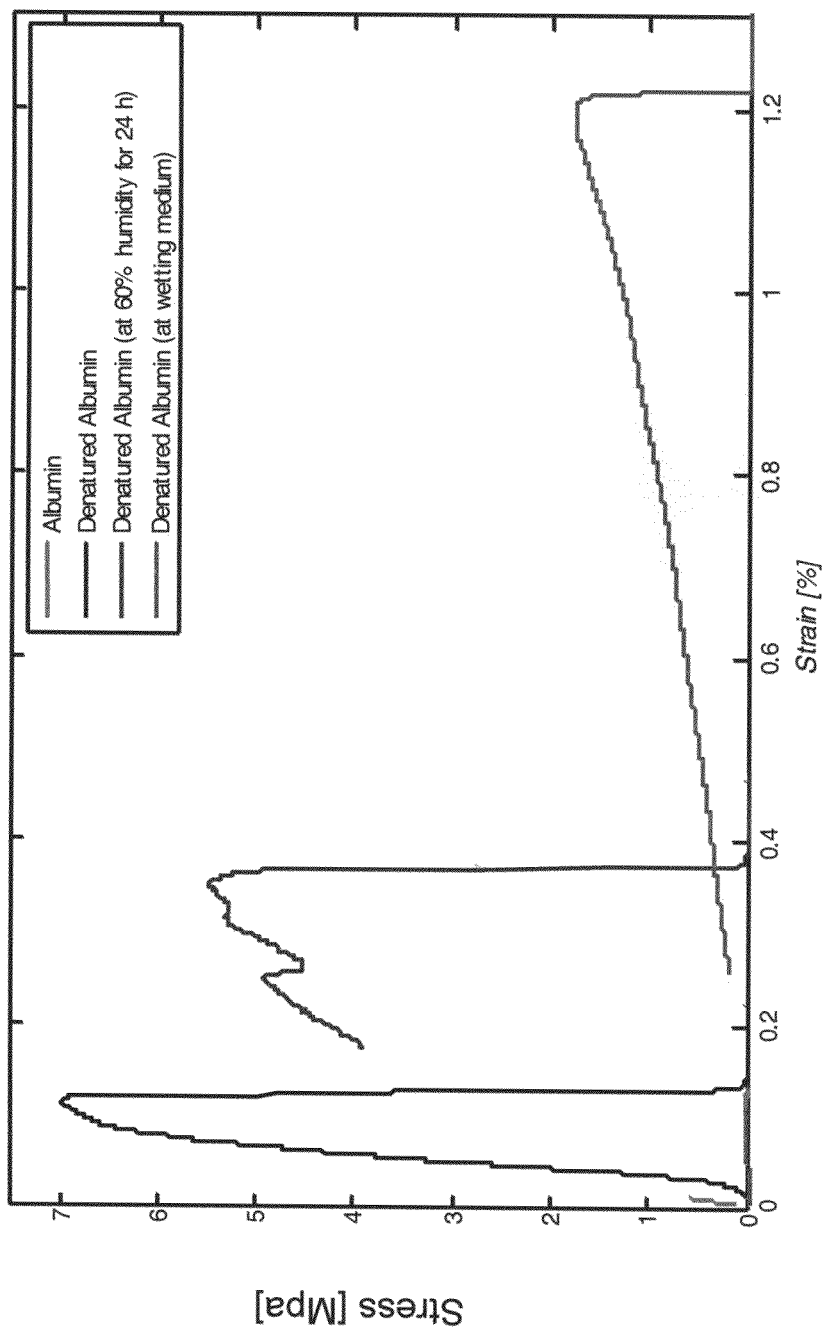
FIG. 5 is a graph depicting tensile stress test result of as-spun fibers: Albumin (red plot)—a sample from aligned fibers mat (fabric); Denatured albumin (black plot)—a sample of a fabric after thermal curing; Denatured albumin at 60% humidity for 24 hours (blue plot)—a sample of a fabric which was in a humid environment (60% humidity) for 24 hours; Denatured albumin (at wetting medium) (green plot)—a sample of a fabric sample that was wetted. The Y axis: Stress [MPA]; the X axis: Strain %.

FIG. 5 presents a typical stress-strain curve of 4 samples: a) a sample from aligned fibers mat (fabric), b) denaturized fabric sample by thermal curing, c) a fabric sample which was in humid environment (60% humidity) for 24 hours, and d) a fabric sample that was wetted. Based on twenty different tests, it was found that for the as-spun fibers the ultimate strength $\sigma_y = \sigma_{max} = 1.1$-$1.3$ MPa. For the denaturized material, E=45-65 MPa and the ultimate tensile strength $\sigma_y = \sigma_{max} = 1.6$-$2.0$ MPa. In all the experiments with the denaturized samples, the maximal strain attained was $\sigma_{max} = 0.1$-$0.18$ (10-18%). It should be noted that Young's modulus is not measured using a clip-on extensometer or strain gauge (that would influence the measurement). As for the nanofibers, this parameter is estimated from the load-displacement curve, and therefore subject to experimental scatter. The ultimate stress of the denaturized material is also identified as a macroscopic estimate of the yield stress. A considerable increase in the strain of the denaturized nanofibers compared to that of the denaturized fibers that stayed in a humid environment is observed. The ductility of the nanofibers is very high, of the order of $\epsilon_f \approx 0.38$ (38%), as opposed to that of the denaturized material $\epsilon_b \approx 0.18$ (18%).

Figure 6:
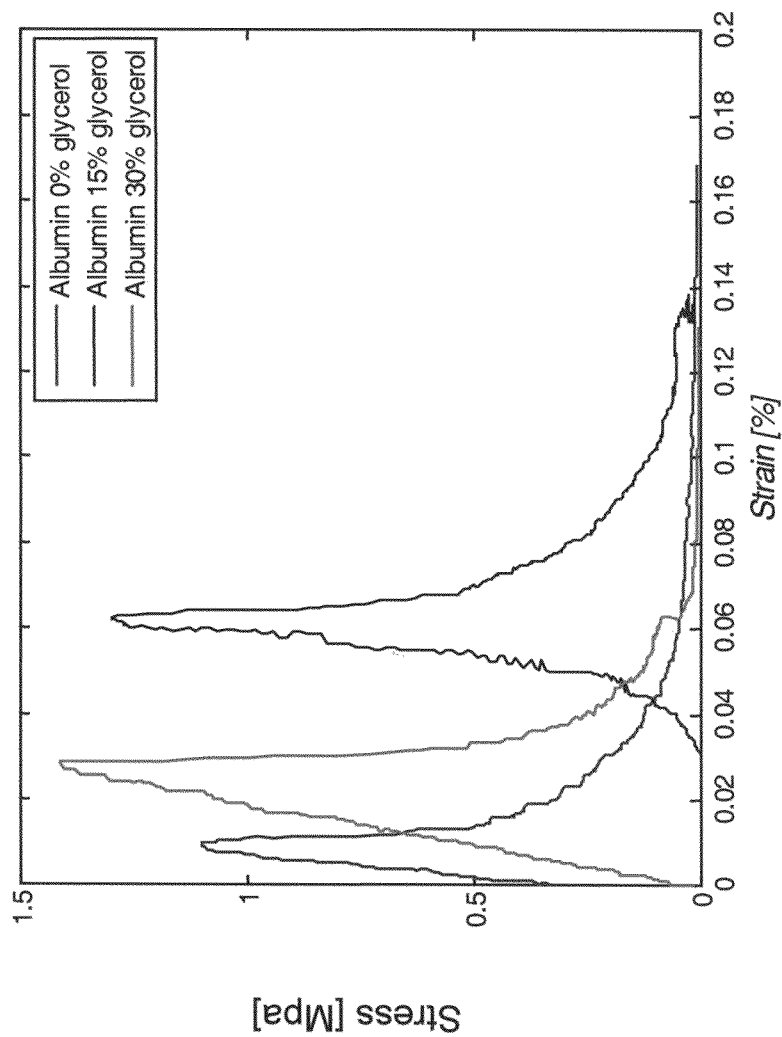
FIG. 6 is a graph depicting tensile stress test result of as-spun albumin nanofibers from Solution B, C and D, showing Strain (%) and Stress MPa.

The quantity of the glycerol serving as a plasticizer and its influence on the mechanical properties of the albumin fabric is presented in FIG. 6. However, a significant effect of the glycerol on the mechanical properties was not observed in the tensile tests.

Example 2

Albumin Fabrics Support Mammalian Cell Growth and Induce Wound Healing

Experimental Procedures

Cells—Primary cell cultures containing fetal human chondrocytes and neonate BALB/C fibroblasts were cultured, grafted by trypsin and incubated over denatured-cured electrospun albumin-glycerin fabrics treated for 30, 60 and 120 seconds with $O_2$ RF excited plasma, and grown to 28 days. Viability was measured by AlamarBlue assay (Biosource International, Camarillo, Calif., USA) for 24 hours, and read by using the Infinite™ 200 microplate reader (Tecan group Ltd, Switzerland) with excitation at 530 nm and emission at 590 nm. Histology was taken from the cells-Albumin fabric constructs, embedded in paraffin, sectioned and stained with hematoxylin and eosin (H & E).

In-Vivo Analysis of the Adhesiveness and Wound Healing Inducer Characteristics of the Albumin Fabrics:

I. Preparation of Albumin Fabrics for Suturing or Laser Soldering to a Wound Bed:

For laser soldering of the albumin fabrics to a wound bed, the albumin electrospun fibers were produced from solution D which further included indocyanine green (ICG-1 mg/ml, MP Biochemical, Inc). The resulting nonwoven albumin fabrics were cut to discs of 6 mm diameter and 100 micron thickness, using a punch biopsy.

For suturing of the albumin fabrics to a wound bed, the albumin electrospun fibers were produced from solution D not including ICG and were collected as a nonwoven fabric which were cut to discs of 6 mm in diameter and a thickness of 200 microns. The discs were further thermally cured to 85° C. for 1 hour, sterilized in UV for 30 minutes and incubated for five days at 37° C. in Dulbecco's modified Eagle medium (DMEM) containing 10% fetal calf serum and 1% penicillin and Streptomycin (Biological Industries, Bet. Haemek, Israel).

II. Healing of Open Wounds in Experimental Animals—

On the day of operation (open wound induction), 40 BALB/C male mice were anesthetized, and open wounds measuring 5.5 mm in diameter were carefully cut over their dorsum. In the control group (n=5), the open wounds were left untouched. In the sutured group (n=5), the open wounds were covered by two discs of thermally cured albumin-glycerol fabrics which were soaked for 5 days in DMEM prior to suturing. In the laser soldered group (n=4), two albumin-ICG fabric discs were introduced to the open wound and were covered by one disc of thermally cured albumin-glycerol fabric which was soaked in DMEM. For laser soldering, a GaAs laser (Lumenis, Model 6030, Israel; wavelength λ=830 nm), with a beam spot of 6 mm was activated for 10 seconds over the covered wound and bonded the albumin discs to the open wound bed. The parameters which were measured to evaluate the success of laser soldering as compared to suturing included: time of procedure, macroscopical results, and histological results.

Experimental Results

The Albumin-Glycerol Fabric Supports Growth of Mammalian Cells—

Figure 7:
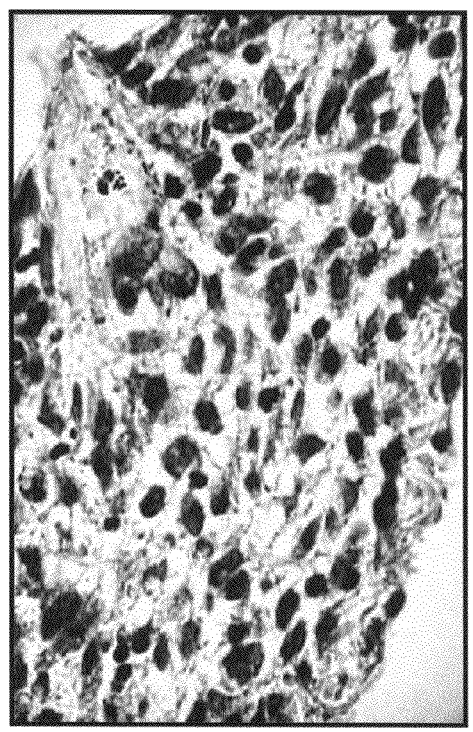
FIG. 7 is a microscopic image of chondrocytes cultured for 14 days over the thermally cured albumin-glycerin fabric. The fabric supports the formation of a cartilage-like tissue (H&E staining, Magnification×1000).

The cured albumin-glycerol fabrics were capable of supporting the formation of cartilage-like tissue when chondrocytes were seeded and cultured thereon (FIG. 7). In addition, the cured albumin-glycerol fabrics were capable of supporting the formation of a skin substitute when skin fibroblasts were seeded and cultured thereon (data not shown). It is possible to improve the albumin fabric cell friendliness to fibroblasts by subjecting the fabric to RF excited oxygen plasma for 60 seconds (data not shown).

The Albumin Fabrics can be Laser Bonded to a Tissue for Closure of Open Wounds—

The albumin fabric discs can serve as open wound coverage by bonding the discs to the recipient site by sutures, laser soldering or adding a biological adhesive. While the suturing procedure takes 320±20 seconds for 4 stitches and provides a peripheral bonding of the discs to the wound edges, the laser bonding procedure takes exactly 10 seconds and provides a complete surface to surface bonding and immediate complete wound sealing. Macroscopic results demonstrate the ability of the laser bonded albumin fabric to completely seal the wound and prevent a potential problematic gap between the wound bed and the albumin coverage as in the case of suturing. Wound healing is much faster when the wound is covered with the albumin fabric (data not shown) and/or less bacteria/contamination comes in.

Example 3

Production and Standardization of Albumin Fabrics

Figure 8:
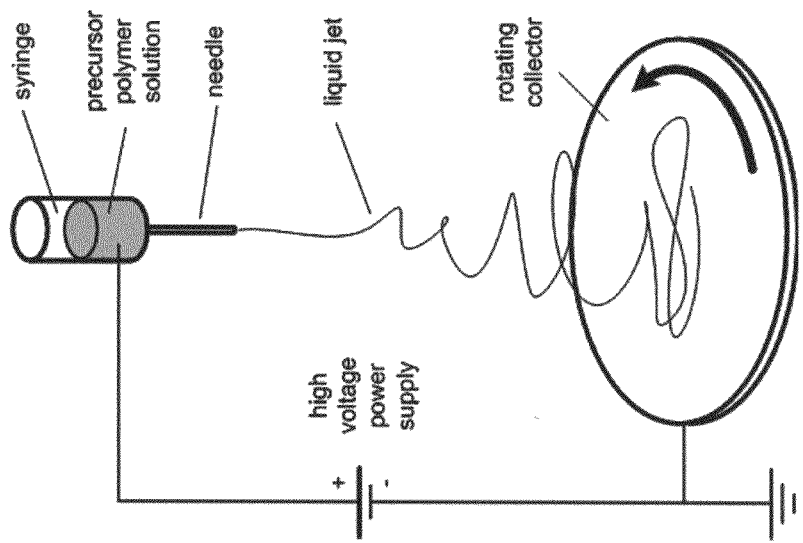
FIG. 8 is a schematic illustration depicting the electrospinning apparatus with horizontal collecting electrode.

Experimental Results
Electrospinning of Albumin Nanofibers—
was performed using an electrospining apparatus as schematically shown in FIG. 8. The non-woven albumin-based ribbon was collected on a vertical rotating wheel for 1 hour and the samples were denaturized by thermally curing to temperatures up to 85° C. in 85-95% humid atmosphere for 1 hour as described under "General Materials and Experimental Methods".

Albumin-Based Fabrics Production and Standardization—
Albumin based non-woven electrospun fabrics were made by employing different solutions containing albumin and glycerin (see exemplary fabrics in FIGS. 9*a-c*). The degree of porosity was 85%±6%, and the fiber thickness was 800±100 nm. The average pore size was 14±2 μm in length and 5±1 μm in width. A typical fabric was made from four layers (~200 μm) and each layer width was 50±15 μm (FIG. 9*c*).

Biomechanics of Albumin Fabrics in Dry and Wet Environments—

Albumin nanofibers with an average diameter of 720, 800 and 900 nm were mechanically tested by tensile testing (uniaxial stretching) of ribbon of aligned electrospun nanofibers by employing a D'Essais Test machine equipped with a 5 kN load cell. The results were validated by employing an Instron testing machine (Instron 4483, Instron Corp., Canton, Mass.) equipped with a 5 kN load cell. Albumin-based fabrics with different concentrations of glycerol were tested for tensile strength and ductility in dry and wet environments. The results are summarized in Table 1, hereinbelow. The addition of 15% glycerol improved the tensile strength, the rigidity and ductility of the albumin-based fabric (p<0.05). The addition of 30% glycerol did not improve any of these parameters. Nevertheless, thermal curing of the 30% glycerol-albumin fabric improved all these parameters compared with uncured 30% glycerol-albumin fabric. The cured-denatured 30% glycerol-albumin fabric kept its structure in water and became very ductile while maintaining sufficient tensile strength comparable to synthetic electrospun fabrics such as PCL and PLGA.

TABLE 1

| Fabric type | No. of Samples (N) | Tensile strength in MPa | Statistics compared to fabric with glycerin content | | | |
|---|---|---|---|---|---|---|
| | | | 0% | 15% | 30% | 30% denatured |
| Tensile strength measurements | | | | | | |
| 0% glycerin | 7 | 1.14 (±0.37) | *** | <0.05 | *** | <0.05 |
| 15% glycerin | 9 | 3.57 (±1.03) | <0.05 | *** | <0.05 | *** |
| 30% glycerin | 7 | 1.42 (±0.35) | *** | <0.05 | *** | <0.05 |
| 30% glycerin denatured | 5 | 4.9 (±2.86) | <0.05 | *** | <0.05 | *** |
| 30% glycerin denatured in water | 5 | 1.66 (±0.16) | *** | <0.05 | *** | <0.05 |
| Young's module measurements | | | | | | |
| | | Young's module in MPa | | | | |
| 0% glycerin | 7 | 88 (±48) | *** | <0.05 | *** | <0.05 |
| 15% glycerin | 9 | 154 (±60) | <0.05 | *** | <0.05 | *** |
| 30% glycerin | 7 | 64 (±19) | *** | <0.05 | *** | <0.05 |
| 30% glycerin denatured | 5 | 103 (±38) | <0.05 | *** | <0.05 | *** |
| 30% glycerin denatured in water | 5 | 1.1 (±0.33) | <0.05 | <0.05 | <0.05 | <0.05 |

| Fabric type Per glycerin content in % | No. of Samples (N) | % elongation before failure | Statistics compared to fabric with glycerin content | | | |
|---|---|---|---|---|---|---|
| | | | 0% | 15% | 30% | 30% denatured |
| Elongation measurements | | | | | | |
| 0% glycerin | 7 | 3.5% (±2.2%) | *** | <0.05 | *** | <0.05 |
| 15% glycerin | 9 | 6.1% (±2.7%) | <0.05 | *** | *** | <0.05 |
| 30% glycerin | 7 | 4.4% (±2.3%) | *** | *** | *** | <0.05 |

TABLE 1-continued

| | | | | | | |
|---|---|---|---|---|---|---|
| 30% glycerin denatured | 5 | 12.2% (±3.5%) | <0.05 | <0.05 | <0.05 | *** |
| 30% glycerin denatured in water | 5 | 136% (±15%) | <0.05 | <0.05 | <0.05 | <0.05 |

Table 1: Mechanical parameters of albumin-based fabrics with different glycerin content in dry and wet environments. One-way Analysis of Variance (ANOVA) with repeated measurements was applied. Statistically significant differences were considered at $p < 0.05$. Glycerin content of 15% improved the albumin-based fabric strength (3.57 ± 1.03 MPa) compared to 0% glycerin and 30% glycerin content. The addition of 15% glycerin improved the rigidity (young's module) and the ductility (elongation) of the fabric compared with albumin-based fabric with no glycerol at all. Thermal curing of the albumin-based fabric containing 30% glycerin improved the strength, the rigidity and ductility of the fabric compared with uncured albumin-based fabric containing 30% glycerin. The wet thermally cured denatured fabric containing 30% glycerin became 33% weaker (1.1 ± 0.33 MPa) and 100 folds more ductile compared with the dry fabric. The water enabled the fabric to elongate to 136% of its original length while maintaining appreciable strength.

Manipulation of the Fabric's Characteristics

Treatment of Albumin with β-Mercaptoethanol—

Treatment of albumin with β-mercaptoethanol (using solution D) prior to electrospinning (n=13) resulted in a highly strong fabric with tensile strength of 34.9±6 MPa, a young's module of 1140±389 MPa and elongation of 25% (±14%). In water, this fabric strength (n=9) decreased by 74% (9.2±3 MPa), the young's module decreased to 1.4% (16.2±5.4 MPa) and ductility improved by almost 3 folds (74% instead of 25%). The β-mercaptoethanol treated albumin-based fabric in water was 5.5 times stronger and 1.8 times less ductile compared with denatured 30% glycerin-albumin fabric in water.

Plasma Etching—

Figures 10A, 10B, 10C:
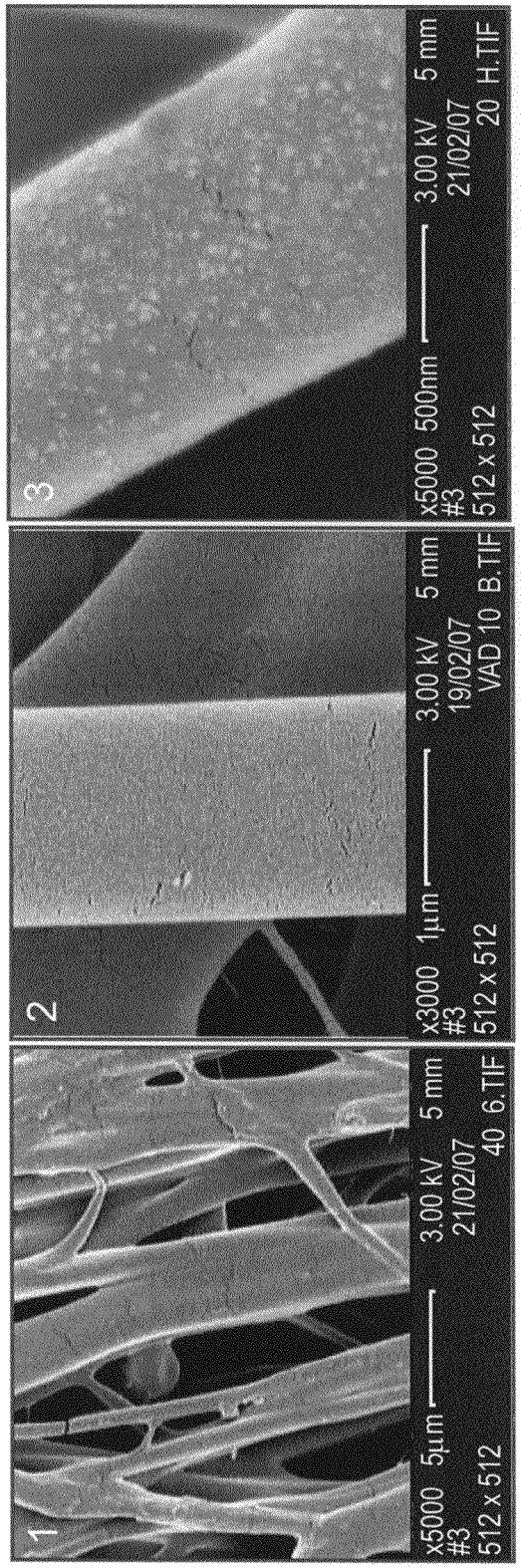
FIGS. 10a-c are SEM images depicting oxygen plasma etching by oxygen of albumin based fabrics.

Albumin-based fabrics made from solution D were etched by reactive ion etching (RIE) process using oxygen as the reactive gas. The oxygen plasma is known to be adequate for etching organic materials. In this process, the oxygen atoms extracted hydrogen atoms from the polymer chain to form radicals. The radicals then reacted with the oxygen molecules to form volatile products ($H_2O$) which were removed from the chamber by either high-temperature conditions or the bombarding plasma flow. The electrospun nanofibers were placed on a 2-inch silicon wafer and inserted into the plasma chamber. The etching was performed using a PDE 301 planar plasma etcher (LFE Corp., Clinton, Mass.), at 50 W and 10 $cm^3$/min oxygen volumetric flow rate. The exposure time ranged from 30 seconds to 120 seconds. As seen in FIG. 10a-c, the topography of the albumin-based fibers was significantly changed by the plasma etching process for 120 seconds.

Wettability and Water Droplet Contact Angle Measurement—

Sessile droplet of double distilled water (DDW) was poured at the centre of each albumin-based fabric. Droplet evolution in time was imaged with an electronic camera (MotionScope—Redlake Imaging Corporation). The water contact angle ($\theta w$) was determined at time 0' after the placing of the droplet. The camera speed was 2000 f.p.s. and the shutter speed 0.05 ms. The camera was equipped with a 70-180 mm, f/4.5 zoom lens. The light source (v) (400 W HMI lamp with Dedolight DEB400D electronic ballast) was placed against the camera along its line of sight. Five different fabrics were evaluated for water contact angle: (1) Albumin-Glycerol-β-mercaptoethanol based fabric, (2) untreated albumin-based fabric and albumin-based fabric treated by $O_2$ plasma etching for (3) 30, (4) 60 and (5) 120 seconds.

Contact angle of albumin-based fabrics was measured. On extremely hydrophilic surfaces, a water droplet will immediately spread (an effective contact angle $\theta w=0°$). This occurs for surfaces that have a large affinity for water. On many hydrophilic surfaces, water droplets exhibit contact angles of $\theta w=10°-30°$. On highly hydrophobic surfaces, which are incompatible with water, one observes a large contact angle ($\theta w=70°-90°$). Some surfaces such as a bird feather have water contact angles as high as 150° or even nearly 180°.

The water droplet contact angle $\theta w$ decreased (as a function of spreading and absorbing by the fabric) by 20% within 40 seconds over the albumin-based fabric treated by plasma etching for 30" and 60" seconds (data not shown). The water droplet contact angle $\theta w$ decreased (droplet spreading and absorbance) over the albumin-based fabric treated by plasma etching for 120 seconds by 65% and β-mercaptoethanol by 32% within 2 seconds (data not shown). No change in the contact angle was seen over the untreated albumin fabric within 40 seconds (data not shown).

Thus, the thermally cured albumin-based fabric had almost no surface water absorbance and a contact angle of $\theta w=109°$ (data not shown). $O_2$ plasma etching for short periods improved the water absorbance rate and increased the contact angle to $\Theta w>120°$ (data not shown). $O_2$ plasma etching for longer period further improved the water absorbance rate but did not influence the contact angle of the albumin-based fabric (data not shown). The β-mercaptoethanol reduced the contact angle of the albumin-based fabric to $\theta w=104°$ and improved the water absorbance rate (data not shown).

Example 4

The Albumin Fabrics Diminish Bacterial Adhesion Thereto but are Suitable for Culturing of Cells-of-Interest Evaluation of bacterial adhesion and biofilm formation (Vuong C, et al. Increased colonization of indwelling medical devices by quorum-sensing mutants of *Staphylococcus epidermidis* in vivo J Infect Dis 2004; 190:1498-1505) over different types of biomaterials-scaffolds and albumin-based non-woven fabrics was performed using fluorescence techniques.

Experimental Procedure

In-Vivo Analysis of the Bacterial Adhesion to Albumin Fabrics and Generation of Biofilms:

I. Electrospun Biomaterials-Scaffolds Preparation—

Electrospun strips made of poly(D,L-lactide-co-glycolide) (PLGA 50:50) and Poly(E-caprolactone) (PCL) served as reference to electrospun thermally cured UV treated albumin-based fabrics made of solution D. Each of the strips (PLGA, PCL & Albumin) was trimmed to form discs of 6 mm in diameter and about 200 microns in width. The discs were placed within a 48 microplate wells, rinsed in PBS twice and left for further bacterial seeding. Six discs were used per each type of fabric and for each biofilm or adhesion measurement.

II. Seeding Procedure—

Two strains of *S. aureus* gram positive bacterial cells were used: (1) Wild type RN6390 with chloramphenicol resistant plasmid and (2) *S. aureus* #1743 carrying a plasmid encoding the egfp (Enhanced Green Fluorescent protein) reporter gene with the chloramphenicol resistant gene. After overnight culture, *S. aureus* strains harboring the recombinant plasmids were diluted 1:100 in Trypticase Soy Broth (TSB) containing chloramphenicol (10 µg/ml) and grown at 37° C. with shaking at 250 rpm.

III. The Adhesion Test—

For the adhesion tests, the bacteria were harvested in stationary phase, diluted in TSB to an optical density of 0.2 OD at a wavelength of 600 nm and 200 µL of bacterial suspension containing $1 \times 10^{10}$ bacteria/ml were plated on the different electrospun fabrics which were placed in a 48 wells plate. After 60 minutes, the fabrics were rinsed three times with PBS. The bacteria adsorbed on the substrate were visualized using an inverted fluorescence microscope and photographed using a digital camera (DP70, Olympus). The fluorescence intensity from each specimen was measured using a fluorescence microplate reader (Infinte 200, Tecan, Austria) in the 48-well plates at wavelengths of 480 and 530 nm for emission and excitation, respectively. The obtained fluorescence signals from the egfp carrying strain #1743 was deducted from the fluorescence signal obtained by the control discs seeded by the wild type *S. aureus* RN6390.

IV. The Biofilm Test—

For the biofilm test, bacteria were seeded over the different discs at concentrations of $5 \times 10^8$ bacteria/ml and the 48 wells plate containing the bacterial seeded discs were incubated overnight at 37° C. for 18 hours. After incubation and biofilm formation, the discs were rinsed three times with PBS and measured in the fluorescence microplate reader.

V. Alamar Blue (AB) Assay for Cells Adhesion and Proliferation—

Initial seeding efficiency (adherence stage) of cells to the albumin-based fabrics who were subjected to plasma etching for 0, 30, 60 or 120 seconds was assessed using a 10% Alamar Blue reduction assay (AB; Biosource, Camarillo Calif.) in DMEM, 24 hours post seeding. Briefly, the albumin-cell construct was incubated with a solution of 10% Alamar Blue in DMEM for 6 hours in the dark. Thereafter, a fluorescence microplate reader (Infinte 200, Tecan, Austria) was used to measure the intensity of the fluorescence signal in the 48-well plates at wavelengths of 530 and 590 nm for emission and excitation, respectively. Cell activity was calculated as the percentage of the net Relative Fluorescence Units of the seeded disks from the average of cell activity in the seeded wells (the control group). For continual assessment of cell proliferation, the AB assay was performed for up to 21 days. After this period, scaffolds were evaluated for cell-fabric adhesion using confocal microscopy as well as for fabric biodigestion by the fibroblasts using regular light microscopy Evaluation of the Albumin Fabrics as Suitable Scaffolds for Cells-of-Interest Cell Culturing Technique Over Electrospun Albumin-Based Fabrics—

On day of seeding, cultured cells obtained from BALB/C neonate skin fibroblasts at about 70%-80% confluence were detached from the flask surface by washing the flask twice with 0.6 ml of 0.25% trypsin; (1) the first time was used to remove debris and unattached cells and (2) after the second washing with trypsin, the flask was incubated at 37° C. for 5 minutes and the cells were observed under the microscope to determine if they were detached (round cells) from the surface. The detached cells were suspended with DMEM, centrifuged (1000 RPM for 3 minutes) and cell sediment was re-suspended in 3 ml of DMEM. A sample from the cell pallet was diluted 1:20000 with PBS and immediately counted in a cell counter (Model ZM, Coulter Electronics, Luton, U.K) at room temperature. Prior to seeding, the albumin fabrics were gently immersed in DMEM for several hours and the extra medium was drained just before cell seeding. For seeding, 0.2 ml containing ~330,000 cells in suspension was poured over each albumin fabric using a pipette. In order to maximize the cells and DMEM absorbance, scaffolds could be dried in a lyophilizer prior to cell seeding. Also, a device based on vacuum was developed with the purpose of forcing cells to penetrate within the scaffold. Scaffolds with cells were then left in the incubator for four hours (adherence phase) for cell attachment. After the adherence phase, scaffolds were entirely covered by DMEM.

Experimental Results

*S. Aureus* Adhesion and Biofilm Formation—

Figure 11:
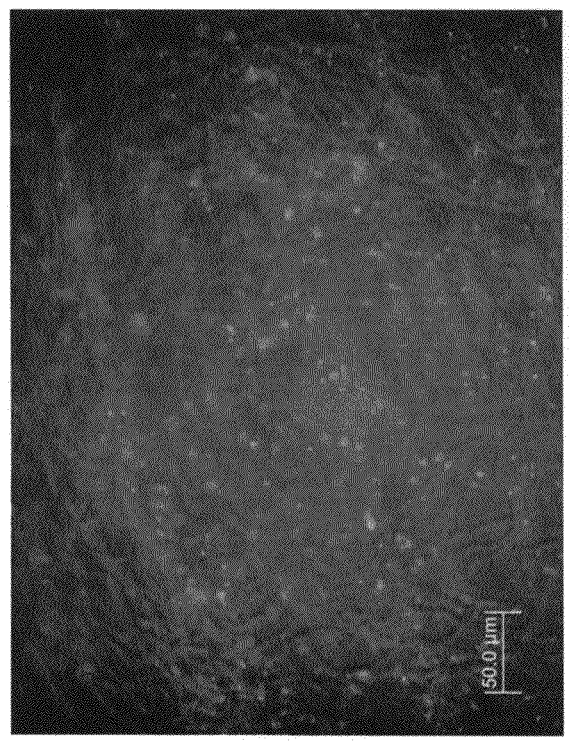
Figure 12:
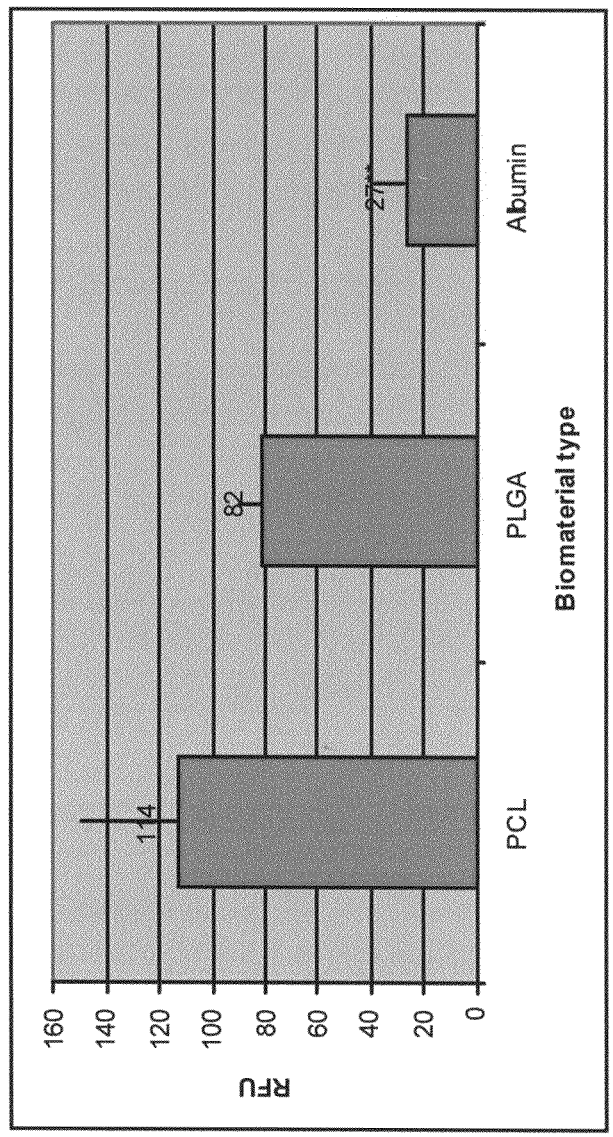

Albumin-based fabric was assessed for adherence and production of a biofilm by *S. aureus* bacteria (FIG. 11) which is the main contaminator of open wounds. As a reference, PCL and PLGA electrospun fabrics were used. Adherence of *S. aureus* to the albumin fabric was statistically significant (p<0.05) lower compared with PCL and PLGA (FIG. 12). With respect to the formation of biofilm, albumin and PLGA had statistically significant (p<0.05) fewer bacteria compared with PCL. It should be emphasized that the initial concentrations of bacteria [Colony Forming Unit (CFU)] for each type of experiments, the adherence and biofilm tests, were $10^{10}$ and $5 \times 10^8$ CFU/ml respectively, which simulates an open infected skin wound.

The Albumin Fabrics of Some Embodiments of the Invention are Suitable for Culturing of Fibroblast Cells—

AB (Alamar Blue-Resazurin, a phenoxazin-3-one dye) is commonly used in cell vitality assays. Primary fibroblasts attachment and viability over albumin-based fabric surfaces modified by $O_2$ plasma etching, was quantified by employing this enzymatic reduction agent (AB) for 21 days follow up period.

$O_2$ plasma etching of albumin-based fabric made from solution D especially for 120 seconds improved both the cell attachment and cell growth rate of the BALB/c primary fibroblasts (data not shown).

The Albumin Fabrics of Some Embodiments of the Invention can be Seeded with Chondrocytes to Form Tissue-Like Matrix—

Human chondrocytes grown for 14 days over the thermally cured albumin-glycerin fabric were able to form an artificial tissue-like matrix (FIG. 7).

Bio-Digestion of Plasma Etched Albumin-Based Fabrics by BALB/C Fibroblasts—

Untreated albumin based fabrics made from solution D and $O_2$ plasma etched albumin-based fabrics for different exposure periods were seeded by BALB/C fibroblasts and cultured for 21 days. All plasma etched treated albumin-based fabrics, especially those treated for 60 seconds, were biodigested by the seeded fibroblasts as opposed to untreated albumin-based fabric. During this process, the plasma etched fabric became thinner and the fibroblasts formed clusters of cells. The fibroblasts became rounded and attained a transparent cytoplasm (data not shown).

Example 5

Anchoring Albumin Grafts to Wound Bed by Laser Bonding

A Ga:As laser soldering system was used. This system utilizes the indocyanine green dye which is immersed in the albumin fabric in order to turn the albumin into "hot glue" that in turn bonds the albumin-based skin substitute to the wound bed. Ex-vivo feasibility experiments were carried out with success over Lucite board.

Experimental Procedures

In-Vivo Anchoring of Albumin Fabrics to Wound Bed in BALB/C Mice:

Electrospun albumin fabrics containing indocyanine green (ICG) were produced in a format of a laser induced adhesive electrospun fabric from solution containing 12% Albumin (1.2 gr), 15% Glycerol (0.18 gr) in TFE to DDW w/w 9:1 and ICG 1 mg to final ICG concentration of 0.72 mg/gr (W/W) fabric, and further were cut into discs of 6 mm diameter and 100 micron thickness, using a punch biopsy. Similar discs with thickness of 200 microns without ICG were prepared and then thermally cured to 85° C. for 1 hour, sterilized in UV for 30 minutes and incubated in DMEM at 37° C. for five days. On the day of operation, 40 BALB/C male mice were anesthetized, and full thickness wounds measuring 5.5 mm in diameter were carefully dissected at the inter-scapular region (between the shoulder girdle) by using biopsy puncher for skin marking and scissors for carefully removing the skin without tempering with the underneath muscle. The animals were allocated to two post operative periods, day 3 and day 5 post operations (20 animals at each time period). Each time period was further divided into four subgroups: The first group served as open wound control (N=5), the second group served as lased control group (n=5). This group included mice with open wounds that were lased by GaAs laser (Lumenis, Model 6030, Israel; wavelength λ=830 nm; Laser power 0.6 Watt; Power density of 1 W/cm2; duration 10 s). In the third group (sutured group; n=5), open wounds were covered by two discs of thermally cured albumin-glycerol fabric soaked in DMEM. The discs were attached to the wound bed by placing four stitches of 6-0 Prolene (Ethicon, Somerville, N.J.) sutures at each disc quadrant. In the fourth laser soldered group (n=5), two albumin—ICG discs were placed over the open wound and were covered by one disc of cured albumin-glycerol mat, soaked in DMEM. Then, a GaAs laser (Lumenis, Model 6030, Israel; wavelength λ=830 nm; Laser power 0.6 Watt; Power density 1 W/cm$^2$; duration 10 s) with a beam spot of 6 mm was activated over the covered wound and bonded the albumin discs to the open wound bed.

Biopsy Fixation and Processing—

On day of sacrifice, animals were euthanized by $CO_2$ gas, and an area of the skin with the repaired wounds in the middle were harvested and stretched over a Whatman paper. Using a small guillotine with sharp knives, one third of each wound was removed, leaving two thirds of the wound with average diameter of ~3.5 mm for histological processing. The samples were placed in a pathological cassette and the cassette were placed in a container of 10% Normal Buffered Formalin (NBF) for four hours and dehydrated in an ascending graded series of ethanol (50%-100%) and cleared in xylene. Then, the processed sections were embedded in paraffin, trimmed into 60 successive sections of 5 μm at the middle of the biopsy sample (the longest diameter), mounted on microscope glass slides (SUPERFROST) and stained for haematoxylin and eosin (H&E) and immunohistochemical stains as follows:

Sections were deparaffinized and rehydrated, in some cases followed by antigen retrieval by heating the sections in ChemMate target retrieval solution (Dako, Glostrup, Denmark) at 90° C. and then incubation with 0.1% trypsin for 15 minutes at 37° C. For general histology, the samples were stained with haematoxylin and eosin (HE). Fibrillar collagen in wound granulation tissue was stained by picro-sirius red. To detect myofibroblasts, sections were blocked with normal goat serum (Dako) before application of antibodies directed against α-smooth muscle actin (Cy3-conjugated α-smooth muscle actin, clone 1A4, Sigma-Aldrich, St. Louis, Mo.).

For immunohistochemistry, sections were blocked with appropriate normal serum (Dako) and incubated with primary antibodies directed against Ki67 (Tec-3, Dako) or F4/80 (Serotec, Oxford, UK), followed by biotin-conjugated secondary antibodies. Then, streptavidin horseradish peroxidase was added and aminoethylcarbazol was used as chromogenic substrate (Dako). If necessary, sections were counterstained with Mayer's haematoxylin (Sigma). Neutrophils and mast cells were visualized by Giemsa and chloroacetate esterase staining according to standard protocols (Leder, 1979). Numbers of Ki67 or chloroacetate esterase positive cells were counted manually. Length and area were determined using DISKUS software (Hilgers, Königswinter, Germany).

Experimental Results

To determine whether lased albumin fabric can produce a surface to surface sealing of an open wound and whether it is able to simulate the attachment of a graft to the wound bed without using mechanical fasteners such as sutures, the present inventors have introduced open skin wounds (5.5. mm in diameter) in experimental animals and albumin fabric discs were attached to the wound bed.

Lased Albumin Fabric can Stimulate Graft Attachments without Mechanical Fasteners—

Figures 14A, 14B:
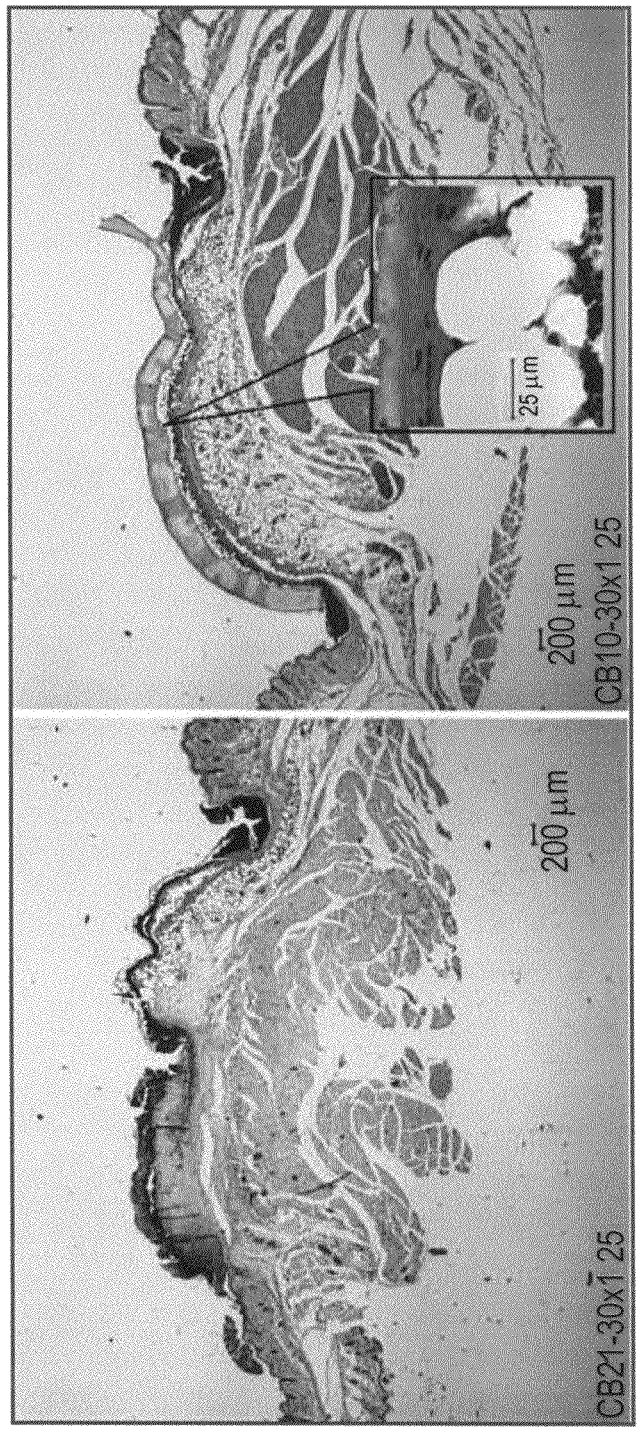
FIGS. 14a-b are histological sections of BALB/C nuchal skin three days post wounding.
Figure 15A:
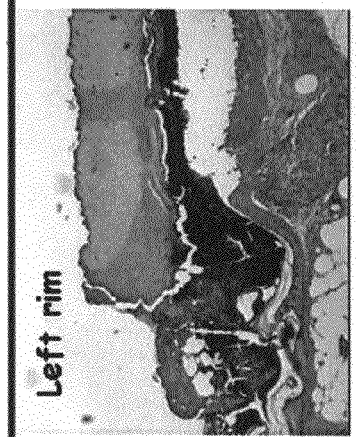
FIGS. 15a-d are histological sections stained with H&E depicting wound closure after 8 days in hyperglycemic Psammomys obesus HED group.
Figure 15B:
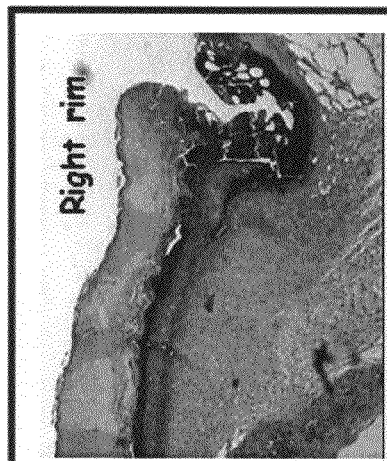
Figure 15C:
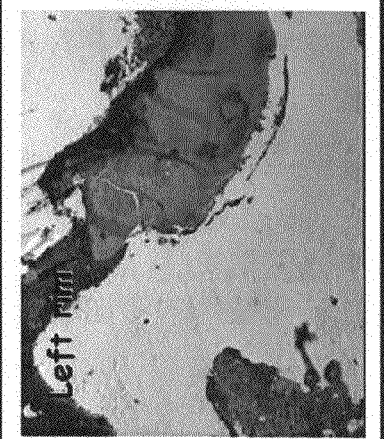
Figure 15D:

In sections that were taken 3 days post operation it is obvious that a mechanism which simulates the attachment of a graft to the wound bed without using mechanical fasteners such as sutures exists (FIG. 14b). The bonded albumin layer formed very fine adhesions with the recipient site below and the albumin graft above (FIG. 14b).

In three days post operation, this lased layer was inhabited by elongated inflammatory cells of unknown nature (FIG. 14b, note the magnifying square) while the upper layer which served as a graft was free of any type of inflammatory cells. In the sutured albumin graft (FIG. 14a), such lased layer did not exist and therefore no migrating inflammatory cells were seen. This thin albumin bonding layer was partially digested after 5 days leaving the upper graft layer in contact with the wound bed (data not shown).

No signs of thermal damage in the form of evaporation-ablation, charred or coagulated tissue were seen in the lased albumin samples (FIG. 14b). Direct lasing of the open wound (control group) with the same laser intensity (power density 2.12 W/cm$^2$ and energy density 21.2 J/cm$^2$) did not create noticeable thermal damage of any kind (data not shown). Moreover, no signs of excessive inflammation or host versus graft reactions in the form of granulomas or foreign bodies were noticed during the 5 days follow-up period (data not shown).

Another safety aspect relates to the ability of the lased albumin glue to serve as a barrier from the hostile environment. On one hand it should hermetically and immediately seal the wound and on the other hand it should not encourage the formation of graft related infections. No signs of infections or pus were noticed (data not shown). The very thin fibers of the electrospun fabric formed a hyalinized, acellular, proteinaceous highly porosive shield. The lased fabric was able to completely seal the wound from the middle portions to the peripheral margins (FIG. 14b) while sutured albumin was not able to seal the very peripheral margins (data not shown). In the open wound group, a fibrin scab was formed and covered the open wound allowing inflammatory cells to inhabit the scab (FIG. 14a).

A potentially important event in open wound closure relates to the pace by which a neoepithelial monolayer is formed. When the neoepithelial layer is not as yet complete, the epithelial tongue's projections (rims) are calculated as the means (±SD) of the two wound edges. Sutured albumin contributed to acceleration in the re-epithelialization rate (2.62±79 mm) compared with open-lased wound (1.7±0.58 mm, post-hoc test p<0.016) and lased-albumin (1.7±0.2 mm, post-hoc test p<0.005) groups while no significant difference was found compared with the open wound group (2.1±0.2 mm) as measured on the 3rd day post operation. This tendency has changed after 5 days. The remaining gap left between the rims was significantly higher in the lased-opened group compared with the sutured albumin group (2.28±2.06 mm and 0.42±0.73 mm, respectively, Post-Hoc p=0.016) but no significant statistical difference was noted between the sutured group and the lased-albumin or the opened group.

These observations of accelerated re-epithelialization pace of sutured albumin discs may be related to the presence of more dermal myofibroblasts in all the groups apart from the sutured group (data not shown). The presence of dermal inflammatory reaction was pronounced in all the different groups as seen by Giemsa staining on days 3 and 5 post operation. No statistical difference was found for mast cells concentrations in all the groups. Nevertheless, at five days post operation, basal, suprabasal and dermal proliferation rate after staining the sections with Ki67 marker (data not shown) in the rim regions was much higher in the sutured group (76.5±2.06 proliferating cells/mm$^2$) then in the open-lased (14.5±7.8 proliferative cells/mm$^2$, Post Hoc p=0.012) and the lased albumin (14.4±21.6 proliferative cells/mm$^2$, Post Hoc 0.008). No significant differences were seen between all the groups and the open unlaced group.

These results demonstrate that laser assisted bonding of electrospun albumin-based fabric is feasible and safe and does not damage the recipient site. Sutured albumin accelerated wound closure rate compared with the lased-albumin group only on day 3 after the operation. This tendency disappeared after 5 days.

Sutured albumin mats did not completely seal the wound as the lased-albumin mats did. The sutured group demonstrated a decrease in wound contraction rate as seen by antibodies directed against a-smooth muscle actin (data not shown). Moreover, the lasing process contributed to reduced proliferation rate compared with sutured wounds. This tendency of the lased-albumin to induce less cell proliferation on day 5 after wounding may contribute in the future to reduction in scar tissue formation (Andriessen M P, et al. Hypertrophic scarring is associated with epidermal abnormalities: an immunohistochemical study. J Pathol 1998; 186(2):192-200).

Example 6

In-Vivo Experiment with Diabetic *Psammomys Obesus* Animals

*Psammomys obesus*, or the Israeli Fat sand rats of the family Cricetidae, subfamily Gerbillinae, develop type II diabetes, including a progression from mild to moderate obesity to hyperglycemia accompanied by the complications of diabetes after dietary modification (high energy, high fat in captivity). The complications include cataracts, skin ulcers, neuropathy, and microangiopathy, mimicking human type II diabetes.

Three different groups of animals were chosen: (1) Normoglycemic animals fed on low energy diet (LE), (2) Animals being fed for 5 weeks with high fat diet and developed hyperglycemia—(Diabetic—HE-D), and (3) Animals which were fed by high energy diet for 5 weeks and did not develop hyperglycemia—(Resistant—HE-R).

Table 2, hereinbelow summarizes the weight gain, blood glucose levels and wound size of the treated animals.

TABLE 2

| Animal No. | Food type | Treatment | weight gain (%) | Ave. BG level (mg/dl) | BG-time 0' (mg/dl) |
|---|---|---|---|---|---|
| 464 | HE-D | Open | 4% | 141 | 60 |
| 481 | HE-D | Open | 9% | 282 | 268 |
| 440 | HE-D | Open | -3% | 271 | 325 |
| 449 | HE-D | Open | 7% | 291 | 253 |
| 452 | HE-D | Albumin | 19% | 293 | 323 |
| 439 | HE-D | Albumin | 4% | 336 | 336 |
| 419 | HE-R | Albumin | 5% | 74 | 87 |
| 667 | HE-R | Albumin | 2% | 75 | 84 |
| 673 | HE-R | Open | 0% | 73 | 84 |
| 485 | HE-R | Open | 12% | 99 | 67 |
| 469 | HE-R | Open | 12% | 88 | 84 |
| 365 | HE-R | Open | -3% | 77 | 77 |
| 492 | LE | Albumin | 17% | 59 | 59 |
| 472 | LE | Albumin | 5% | 66 | 57 |
| 444 | LE | Open | 3% | 58 | 70 |
| 494 | LE | Open | 9% | 64 | 71 |

Table 2: Summary of the weight gain and blood glucose (BG) measurements of each Psammomys obesus animals in the experiment. Normoglycemic animals fed on low energy diet (LE) were animals Nos. 492, 472, 444 and 494; Animals fed on high fat diet and developed hyperglycemia (Diabetic- HED) were animals Nos. 464, 481, 440, 449, 452 and 439; Animals fed on high energy diet but did not develop hyperglycemia (HER) were animals Nos. 419, 667, 673, 485, 469, 365. The type II diabetes induced group (HED) had an average BG level of 269 mg/dl while the diabetic resistant group (HER) had an average BG level of 81 mg/dl. Wound size on day of euthanasia was measured as the function of the long and short axis of the wounds by using an ellipse area equation.

On the day of operation, full thickness wounds measuring 6 mm in diameter were carefully dissected as described in Example 5, hereinabove. In each of the abovementioned groups several wounds were left open and several were covered by lased albumin as described in Example 5, hereinabove, with the exception that the laser bonding procedure took 20 seconds instead of 10 seconds and the electrospun albumin discs were made of a solution containing BSA and β-mercaptoethanol instead of heated denatured albumin discs (data not shown). The animals were kept for 8 days post operation and then skin regions around the wounds were harvested and processed for H&E staining. The results demonstrate accelerated re-epithelialization of the albumin-lased wound in the hyperglycemic HE-D group (FIGS. 15a-d) as well as in the HE-R and LE groups compared with open wounds (data not shown).

Moreover, staining with Toluidine Blue (instead of chloroacetate esterase) revealed increased concentration of mast cells in the laser soldered group compared with the open wound (data not shown), which is related to improved wound healing [Artuc M, et al, Mast cells and their mediators in cutaneous wound healing—active participants or innocent bystanders? Exp Dermatol 1999; 8(1):1-16].

Example 7

Adhesive of Albumin Fabrics to Fascia Strips

Experimental Procedures

Porcine fascia strips (dimensions 5×0.2×30 mm$^3$) were glued together end-to-end in wet conditions with Albumin sheets (dimensions 5×0.18×12 mm) and 10% glutaraldehyde and then subjected to a tensile load in an Instron machine attached to 100 N load cell (FIGS. 16a-c).

Experimental Results

Gluing was achieved within 2 minutes. The average shear strength on the adhesive was τ=~140 kPa and the adherend tensile stress was σ=~700 kPa. The magnitude of the adhesive stress is comparable to the known stress (τ=150 kPa) of an adhesive test of cyanoacrilte (Loctite 4011) bonded to calf pericardium strips (cf. Garcia Paez J. M J. of materials Science: Materials in Medicine, 15, 2004), and are much greater than the adhesive stress known for BioGlue® ($\tau$=40 kPa).

Thus, the albumin-based fabrics adhere to fascia strips within 2 minutes and exhibit shear strength ($\tau$=~140 kPa) and tensile stress ($\sigma$=~700 kPa) which are comparable to industrial cyanoacrylate and 3 fold stronger then Bioglue®.

Example 8

Electrospinning of Albumun via Denaturation with Beta-Mercaptoethanol

Materials and Experimental Methods

Bovine Serum Albumin (BSA) Fraction V was supplied by MP Biomedicals (Israel).

Trifluroethanol (TFE) was purchased from Aldrich-(U.S.A.).

TABLE 3

Solutions used for electrospinning of albumin

| Solution No. | Compositions |
|---|---|
|  | 12% BSA TFE:H$_2$O 9:1 (weight ratio) |
| A0 | 10% BSA TFE:H$_2$O 9:1 + 10 eq/bond β-ME |
| A1 | 10% BSA TFE:H$_2$O 9:1 + 10 eq/bond β-ME + IAA |
| A2 | 10% BSA TFE: Ammonium hydroxide 0.1M 9:1 + 10 eq/bond β-ME + IAA pH ~9 |
| A3 | 10% BSA TFE: Ammonium hydroxide 0.1M 9:1 + 10 eq/bond β-ME pH ~9 |
| A11 | 10% BSA TFE: HCl 0.1M 9:1 + 10 eq/bond β-ME pH ~2 |

Table 3: Composition of the solutions from which the fibers were electrospun. 10 eq/bond β-ME – 10 equivalents (molecules) of β-ME for each S—S bond in the protein.

Electrospinning—

The solutions underwent electrospinning from a 5 ml syringe with a hypodermic needle having an inner diameter of 0.5 mm. The flow rate was Q=0.2-0.5 ml/hour. A copper electrode was placed in the polymer solution and the suspension was spun onto the edge of a grounded collector disk (for more details on electrospinning see Theron A., et al., 2001) and on horizontal disk. The strength of the electrostatic field was E=1.1 kV/cm and the distance between the electrode tip and the edge of the disk (or the horizontal disk) was 12 cm. The linear speed at the edge of the disk collector was V=8.8 m/s. All the experiments were performed at room temperature (about 24° C.), and a humidity of about 50%. The samples stored for 24 hours in a desiccator (humidity of about 30%).

Imaging—

Images of the fibers were obtained using Leo Gemini high resolution scanning electron microscope (HRSEM) at acceleration voltage of 2-4 kV and sample to detector distance of 2-5 mm. The specimens were coated with a thin gold film to increase their conductivity.

For imaging of the fibers' cross-section, the fibers were collected on a rotating wheel following Theron et al.'s approach (Theron, et al., 2001; Nanotechnology 12: 384) and the oriented mat was cut by a special blade designed in our laboratory using liquid nitrogen.

Mechanical Properties—

For tensile measurements the electrospun nanofibers were collected on a grounded rotating disk forming a converging electric field (Theron, et al., 2001; Nanotechnology 12: 384). By this, a strip, 2.5 cm wide, of oriented fibers has been formed. The thickness of this strip was measured by imaging the cross section of the strip which has been cut under liquid nitrogen using a scanning electromicrograph (SEM). Tensile tests were conducted on a Testmashine D'Essais—a uniaxial tension machine designed for small samples. The effective cross section of the strip which takes into account the voids in between the collected fibers in the strip was determined by:

$$\text{cross section area} = a \cdot t \cdot (1-p) \quad (1)$$

Where a is the strip width, t is the measured thickness and p is the porosity which was obtained by weighting the total strip and calculating according to:

$$1 - p = \frac{m}{L \cdot a \cdot t \cdot \rho} \quad (2)$$

Where: m is the mass of the total strip, L is the strip's length and p is the protein density which was taken as 1.4 gr/ml. Each result is an average of 12-15 specimens.

X-Ray Diffraction—

Wide-angle X-ray scattering (WAXS) measurements were performed with a Bruker Nanostar KFF CU 2 K-90 small-angle diffractometer with Cu Ka radiation (0.1542 nm), pin-hole collimation (that yielded a beam 300 μm in diameter), and a 10×10 cm$^2$ two-dimensional position-sensitive wire detector positioned 7 cm behind the examined sample. For the WAXS measurements the fibers were collected on a vertical rotating wheel having a tapered edge forming a thin rope of oriented fibers. This rope was then fixed on an aluminum frame and this frame was mounted in the diffractometer in a way the fibers are perpendicular to the x-ray beam.

Experimental Results

Fibers can be Formed by Albumin and a Reducing Agent—

Bovine serum albumin (BSA) solution was prepared in a mixture of 9:1 (w/w) TFE:H$_2$O as shown in Table 3, hereinabove. Upon the addition of β-mercaptoethanol (β-ME), a reducing agent of disulfide bonds, a remarkable improvement of the electrospinning process was achieved and fibers with an average length ranging from 10 mm-20 cm and a diameter ranging from 100-1500 nm were obtained. The breakage of the disulfide bridges together with the denaturing environment of the TFE, enabled a pronounced expansion of the protein which in turn affects the rheological properties of the solution and its spinnability. The improvement of the process was reflected in the morphology, structure and mechanical properties of the resulting fibers. SEM micrographs of the fibers with β-ME are presented in FIG. 17.

The Albumin Fibers Formed by Electrospinning of an Albumin-TFE-βME Solution Exhibit Excellent Mechanical Properties—

The tensile properties of the different as-spun albumin fibers measured according to the procedure described in the experimental section hereinabove (Example 8), are presented in FIGS. 18a-c. The albumin fibers formed from a solution containing β-ME exhibited mechanical properties which are superior to any known fibers formed of any natural protein. For example, the elastic modulus of the albumin fibers was in the range of 1500-2500 Mpa (FIG. 18a, fibers formed of solutions A0, A3 and A11), and the stress peak was in the range of 20-60 Mpa (see FIG. 18b, albumin fibers formed of solutions A0, A3 and A11).

The Superior Mechanical Properties of the Albumin Fibers Result from Formation of an Albumin Polymer with New S—S Bondings in and Between Albumin Molecules—

The effect of IAA on the albumin fiber was further demonstrated by testing the mechanical properties of the albumin fibers formed with β-ME which were further treated with IAA. IAA is known to react covalently with the sulfuric site of the cysteine residues by alkylation reaction. In the present case, the IAA was added to the solution after the β-ME reacted and broke the disulfides bonds, and hence reacted with the available sulfuric sites. The marked difference in the mechanical properties between the two groups reflects the role of the disulfides bonds in the albumin fiber. While in the absence of IAA the spontaneous reformation of new disulfides bonds, inter bonds in preference, could take place, in the presence of IAA this was prevented. It is suggested then that the inhibition of S—S bridges reformation in the presence of IAA is responsible for the lower strength and stiffness (FIGS. 18a and b, A1 and A2) but allows the larger deformation due to free movement of the molecules as clearly seen in FIG. 18c (A1). In the absence of IAA the fibers exhibit enhanced strength and stiffness with maximum stress and elastic module of about 50-60 MPa and 2 GPa, respectively, due to the reinforcing covalent cross-linking achieved by spontaneously-formed inter S—S bonds. These values are far higher than not only the values reported for the globular hemoglobin electrospun fibers (Barnes, et al., 2006) but also the values reported for fibrous proteins electrospun fibers such as collagen, gelatin, elastin and fibrinogen (Li, et al., 2005; McManus, et al., 2006) and are comparable to natural fibers. Yet, the self S—S cross-linking is apparently not the only reason for the improved properties. A0, A3 and A11 differ in the pH of the solution from which they have been spun. The pH has a multi-effect on the chain conformation, the reduction of S—S bonds and the aggregation of the proteins. The reduction of the disulfides bonds is favorable at basic pH. The amount of intra disulfides bond reduction and thereby inter S—S bridge formation is different at each types of fibers and consequently affects their mechanical properties. Proteomic analysis of A1 and A2 solutions reveals that more cysteine residues were modified by IAA in the basic solution (A2) compared to the neutral one (A1) (data not shown) indicating that more disulfides bonds have been cleaved by the β-ME and consequently were available for new disulfides bonding. On the other hand, it shall be reminded that BSA has the ability to undergo reversible conformation transitions upon changes in pH. At acidic conditions BSA becomes pronouncedly expanded, a conformation termed as E form and the aggregation of the molecules is inhibited since the protein is highly positively charged. Under these conditions, the solution consists of opened elongated and isolated chains, a situation which is most favorable for the spinning process and the stretching of the molecules during the process. Thus, the improved properties of A11 fibers can be assigned to the alignment of the molecules and to the high quality of the spinning process. The different source for the achievement of the improved properties for each type of fiber is well reflected in the typical stress-strain curves presented in FIG. 19. Among the strongest fibers (A0, A3, A11) the high strength of A3 fibers is not accompanied by a drastic reduction in the elongation. A3 fibers are much more ductile and have higher toughness than the other two. In fact the tensile curve of A3 resembles to a typical hard and tough polymer characterized by a yielding point and subsequent cold drawing and moderate strain hardening. This behavior is related to an additional orientation which takes place during the stretching in the necking area. Specimen that attain their maximum orientation right in the beginning of the stretching can not undergo this elongation but rather break right after the elastic linear region of the stress-strain curve as a hard and brittle polymer. This is the case for A11 and A0 fibers. On a neutral pH (as the case of A0) which is closed to the isoelectric point of the protein the molecules tend more easily to aggregate at the solution and even more during the evaporation of the TFE. This aggregation may disturb the electrospinning process and restrict additional orientation during the stretching. A3 fibers, on the other hand, resemble more to a rubber with high degree of S—S cross-linking. During the drawing process the molecules between the cross-linking points which were not aligned in first place can undergo additional orientation. Yet since the density of the cross-linking points is rather high the elongation is limited and although being larger than the other fibers (more than double) is still lower compared to real rubber which is more soft and tough. Ultimately, A3 fibers have a remarkable combination of properties gathering the stiffness of collagen and keratin and extensibility of dragline silk.

Figure 22:
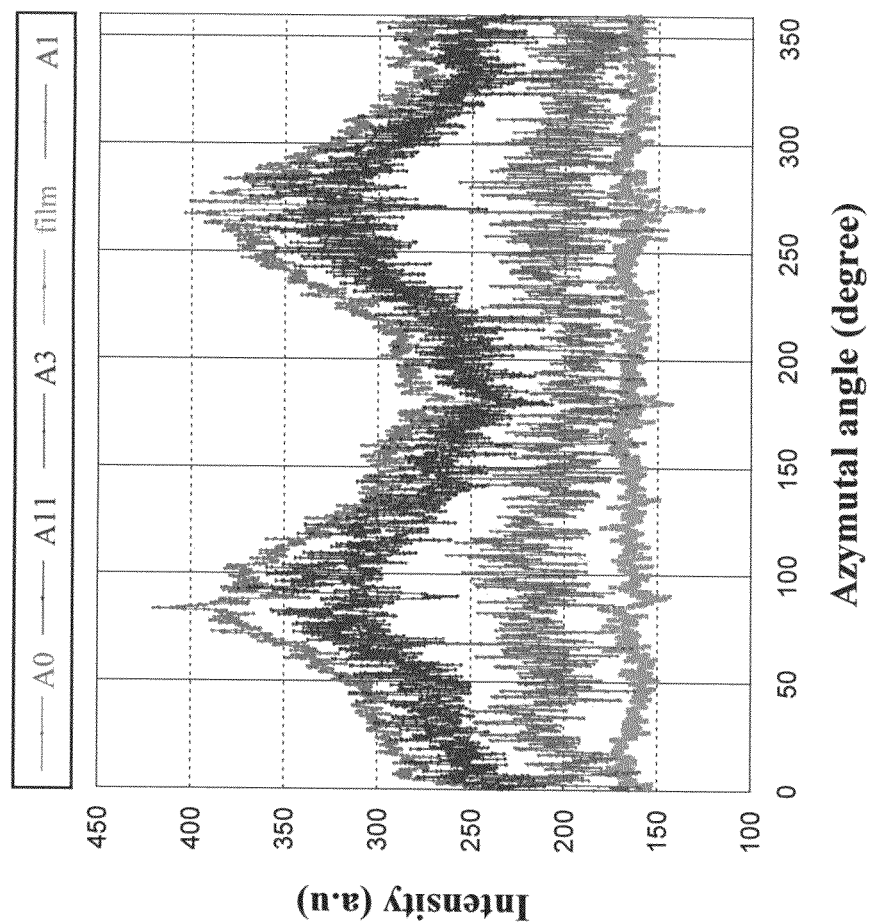

X-ray diffraction patterns of different fibers are shown in FIGS. 20a-e and 21. For full comparison and evaluation of the influence of each component in the solution the diffraction patterns of different films which have been casted from water, TFE/water mixture and TFE/water/β-ME mixture and powder raw protein were recorded as well. The diffraction patterns showing distinct rings indicate that the casted films as well as the nanofibers are crystalline. It is also clearly seen in the 1D patterns that the diffraction peaks' positions reflecting the d-spacing, of all the samples are identical. The patterns are characterized by two Bragg peaks at $2\theta=9.3°$ and $20°$ corresponding to 9.5 Å (inner ring) and 4.4 Å (outer ring) d-spacing respectively. The 4.4 Å d-spacing is suggested to be related to the backbone distance within the α-helix while the larger d-spacing is attributed to lateral inter α-helix packing. This interpretation is supported by previous reports on the x-ray diffraction of natural α-proteins (Arndt and Riley, 1955) and also agrees with the recent structural investigation conducted by Wang and co workers on zein which is a group of alcohol-soluble proteins found in corn endosperm (Wang, et al., 2005). It should be borne in mind that also BSA is a rich α-helix and a globular protein and is dissolved in rich TFE/water mixture similarly to zein proteins (Lai, et al., 1999). These results state that the secondary structure of the protein, the dimension of the helixes and their rearrangement in the solid state is maintained following the dissolution of the protein in TFE, the addition of β-ME which breaks the disulfides bonds. Nonetheless, for the fibers containing β-ME (A0, A3, A11) the inter d-space (inner ring) is slightly oriented as seen by the equatorial arcs while the 4.7 Å d-spacing is totally isotropic as seen in FIG. 22. This difference between the two peaks gives another support to the fact that these peaks are attributed to separate periodic order and are not simply two reflections of the same d-spacing with different order of Bragg law. This result indicates that the crystals or sub-elements made of ordered α-helix segments are preferably aligned along the nanofibers axis. In all the other samples, including the fibers containing IAA (A2) which prevents the reformation of disulfides bonds as was described above, there is not any preferential orientation. Hence, the electrospinning process together with the cleavage of the intra disulfides bonds and the reformation of new disulfides bonds which are probably inter bonds are advantageous for the preferential orientation.

The degree of crystallinity in the electrospun fibers may also explains the improved mechanical properties. This is in contrast to the results given for silk fibers electrospun from aqueous solution. In this case it was demonstrated that the silk remained amorphous and no typical peak found in natural silk, assigning to crystalline β-sheet, was observed (Wang, et al., 2004; Chen, et al., 2006). However, the same silk electrospun from fluorinated alcohol solution (TFE), exhibited a crystalline diffraction pattern (Zarkoob, et al., 2004). It is important though to note that the rings of A1 and A11 fibers are more diffused reflecting that the degree of crystallinity is lower since the presence of the attached IAA in A1 and the electrostatic repulsion in A11 restrict the formation of ordered aggregation.

In summary, fibers with controllable and improved mechanical properties made of solely globular protein have been successfully electrospun. The control of their respond to tensile stress was achieved by manipulating the conformation of the protein chains, their electronic charge and the reduction of the self disulfides bonds and/or the recombination of new cross-linking ones. These parameters could be regulated by the denaturation of the TFE environment, the presence of disulfides reduction agent and/or pH during the electrospinning process. This method enabled the unfolding, expanding and opening of the protein molecules and reformation of desired S—S bonds during the spinning and solidification stages. The balance between these operational parameters provides the ability to control the unfolding of the protein chains, degree of cross-linking, degree of crystallinity, aggregation propensity and orientation of the helix-helix interactions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Peters T Jr. All about albumin: biochemistry, genetics, and medical applications. San Diego: Academic Press, 1996: 248-49
2. Peters T Jr. All about albumin: biochemistry, genetics, and medical applications. San Diego: Academic Press, 1996: 79-127.
3. Simhon D, et al. Closure of skin incisions in rabbits by laser soldering: I: Wound healing pattern. Lasers Surg Med 2004; 35:1-11
4. Brosh T, et al. Closure of skin incisions in rabbits by laser soldering II: Tensile strength. Lasers Surg Med 2004; 35:12-17.
5. Simhon, D., et al. Immediate Tight Sealing of Skin Incisions using an Innovative Temperature Controlled Laser Soldering Device: in-vivo Study in Porcine Skin, Ann. Surg. In-Press (2006)).
6. Peters T Jr. All about albumin: biochemistry, genetics, and medical applications. San Diego: Academic Press, 1996: 289
7. WO2005037108 to Waserman I, Dror M and Simhon D.
8. A. Theron, E. Zussman, A. L. Yarin, "Electrostatic field-assisted alignment of electrospun nanofibers", Nanotechnology J., 12, 3: 384-390, 2001.
9. Arndt, U. W., and D. P. Riley. "The Structure of Some Proteins as Revealed by an X-Ray Scattering Method." Phylos. Trans. R. Soc. Lon. A 247(1955): 409-439.
10. Askura, T., K. Adachi, and E. Schwrtz. "Stabilizing Effect of Various Organic Solvents on Proteins." The Journal of Biological Chemistry 253, no. 18(1978): 6423-6425.
11. Banerjee, T., and N. Kishore. "Does the Anestetic 2,2,2,-Trifluoroethanol Interact with Bovine Serum Albumin by Direct Binding or by Solvent-Mediated Eggects? A calorimetric and Spectroscopic Investigation." Biopolymers 78(2005): 78-86.
12. Barnes, C. P., et al. "Feasibility of Electrospinning the Globular Proteins Hemoglobin and Myoglobin." J. Eng. Fibers and Fabrics 1, no. 2(2006): 16-28.
13. Bhattarai, N., et al. "Alginate-Based Nanofibrous Scaffolds:Structural, Mechanical and Biological Properties." submmited (2006).
14. Cammers-Goodwin, A., et al. "Mechanism of Stabilization of Helical Conformations of Polypeptides by Water Containing Trifluoroethanol." J. Am. Chem. Soc. 118(1996): 3082-3090.
15. Chen, C., et al. "Preparation of Non-Woven Mats from all-Aqueous Silk Fibroin Solution with Electrospinning Method." Polymer 47(2006): 6322-6327.
16. Dror, Y., et al. "One-Step Production of Polymeric Micro-Tubes via Co-Electrospinning." Small 3, no. 6(2006): 1064-1073.
17. Foo, C. W. P., et al. "Novel Nanocomposites from Spider Silk-Silika Fusion (Chimeric) Proteins." PNAS 103, no. 25(2006): 9428-9433.
18. Hong, D. P., et al. "Clustering of Fluorine-Substituted Alcohols as a Factor Responsible for Their Marked Effect on Proteins and Peptides." J. Am. Chem. Soc. 121(1999): 8427-8433.
19. Jia, H., et al. "Enzyme-Carrying Polymeric Nanofibers Prepared via Electrospinning for Use as Unique Biocatalysts." Biotechnol. Prog. 18(2002): 1027-1032.
20. Jiang, H., et al. "Optimization and Characterization of Dextran Membranes Prepared by Electrospinning." Biomacromolecules 4(2004): 326-333.
21. Kumar, Y., S. Muzammil, and S. Tayyab. "Influence of Fluoro, Chloro and Alkyl Alcohols on the Folding Pathway of Human Serum ALbumin." J. Biochem. 138(2005): 335-341.
22. Kwon, I. K., and T. Matsuda. "Co-Electrospun Nanofiber Fabrics of Poly(L-lactide-co-e-caprolactone) with Collagen or Heparine." Biomacromolrcules 6(2005): 2096-2105.
23. Lai, H. M., P. Geil, and G. W. Padua. "X-Ray Diffraction Characterization of the Structure of Zein-Oleic Acid Films." J. Appl. polym. sci. 71(1999): 1267-1281.
24. Li, M., et al. "Electropsun Protein Fibers as Matrices for Tissue Engineering." Biomaterials 26(2005): 5999-6008.
25. Luong-Van, E., et al. "Controleed Release of Heparine from Poly(e-caprolactone) Electrospun Fibers." biomaterials 27(2006): 2042-2050.
26. Luu, Y. K., et al. "Characterization of an Electrospun Poly(lactide-co-glycolide) and Block Copolymer-based Nanostrucured Matrix for DNA Delivery."
27. Matthews, J. A., et al. "Electrospinning of Collagen Nanofibers." Biomacromolecules 3(2002): 232-238.
28. McManus, M. C., et al. "Mechanical properties of Electrospun Fibrinogen Structures." ActaBiomaterialia 2(2006): 19-28.
29. Min, B. M., et al. "Electrospinning of Silk Fibroin Nanofibers and its Effect on the Adhesion and Spreading of Normal Human Keratinocytes and Fibroblast in Vitro." Biomaterials 25(2004): 1289-1297.
30. Putthanarat, S., et al. "Electrospun *Bombyx Mori* Gland Silk." polymer 47(2006): 5630-5632.

31. Salalha, W., et al. "Encapsulation of bacteria and viruses in electrospun nanofibres." Nanotechnology 17, no. 18(2006): 4675-4681.
32. Scheibel, T. "Protein Fibers as Performance Proteins: Mew Technology and Applications." Current Opinion in Biotechnology 16(2005): 427-433.
33. Sell, S., et al. "Review: Extracelluar Matrix Regenerated: Tissue Engineering via Electrospun Biomimetic Nanofibers." Polym. Int. 56(2007): 1349-1360.
34. Shin, H. J., et al. "Electrospun PLGA Nanofiber Scaffolds for Articular Cartilage Reconstruction: Mechanical Stability, Degradation and Cellular Responses Under Mechanical Stimulation in Vitro." J. Biomater. Sci. Polymer Edn. 17, no. 1-2(2006): 103-119.
35. Stephens, J. S., et al. "Effects of Electrospinning and Solution Casting Protocols on the Secondary Structure of a Genetically Engineered Dragline Spider Silk Analogye Investigated via Fourier Transform Raman Spectroscopy." Biomacromolecules 6(2005): 1405-1413.
36. Theron, A., E. Zussman, and A. L. Yarin. Nanotechnology 12(2001): 384. Thomas, E., et al. "Nanofibers From Natural and Inorganic Polymers Via Electrospinning." International Nonwovens Journal 14, no. 3(2005): 12-18.
37. Wang, M., et al. "Mechanical Properties of Electrospun Silk Fibers." Macromolecules 37(2004): 6856-6864.
38. Wang, Y., et al. "Effects of Processing on the Strucutre of Zein/Oleic Acid Films Investigated by X-Ray Diffraction." Macromol. Biosci. 5(2005): 1200-1208. Wnek, G. E., et al. "Electrospinning of Nanofiber Fibrinogen Structures." Nano Letters 3, no. 2(2003): 213-216.
39. Xie, J., and Y. L. Hsieh. "Ultra-high Surface Fibrous Membranes from Eelectrospinning of Natural Proteins: Casein and Lipase Enzyme." J. Mater. Sci. 38(2003): 2125-2133.
40. Zarkoob, S., et al. "Structure and Morphology of Electrospun Silk Nanofibers." Polymer 45, no. 11(2004): 3973-3977.

What is claimed is:

1. A fiber comprising a polymer which comprises molecules of serum albumin covalently connected to at least two other molecules of serum albumin by disulfide bonds, the fiber comprising more than 50% serum albumin.

2. A fabric comprising the fiber of claim 1.

3. The fiber of claim 1, characterized by an elastic modulus of at least 1000 MPa.

* * * * *

SEQUENCE LISTING

<160> NUMBER OF SEQ ID NOS: 9

<210> SEQ ID NO 1
<211> LENGTH: 609
<212> TYPE: PRT
<213> ORGANISM: Homo sapiens

<400> SEQUENCE: 1

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240
```

```
Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 2
<211> LENGTH: 608
<212> TYPE: PRT
<213> ORGANISM: Mus musculus

<400> SEQUENCE: 2
```

```
Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430
```

Val Arg Tyr Thr Gln Lys Ala Pro Gln Val Ser Thr Pro Thr Leu Val
                435                 440                 445

Glu Ala Ala Arg Asn Leu Gly Arg Val Gly Thr Lys Cys Cys Thr Leu
450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
                500                 505                 510

Ser Ala Leu Thr Val Asp Glu Thr Tyr Val Pro Lys Glu Phe Lys Ala
                515                 520                 525

Glu Thr Phe Thr Phe His Ser Asp Ile Cys Thr Leu Pro Glu Lys Glu
                530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
                580                 585                 590

Ser Thr Glu Gly Pro Asn Leu Val Thr Arg Cys Lys Asp Ala Leu Ala
                595                 600                 605

<210> SEQ ID NO 3
<211> LENGTH: 608
<212> TYPE: PRT
<213> ORGANISM: Canis familiaris

<400> SEQUENCE: 3

Met Lys Trp Val Thr Phe Ile Ser Leu Phe Phe Leu Phe Ser Ser Ala
1               5                   10                  15

Tyr Ser Arg Gly Leu Val Arg Arg Glu Ala Tyr Lys Ser Glu Ile Ala
                20                  25                  30

His Arg Tyr Asn Asp Leu Gly Glu Glu His Phe Arg Gly Leu Val Leu
                35                  40                  45

Val Ala Phe Ser Gln Tyr Leu Gln Gln Cys Pro Phe Glu Asp His Val
50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
                85                  90                  95

Lys Leu Cys Thr Val Ala Ser Leu Arg Asp Lys Tyr Gly Asp Met Ala
                100                 105                 110

Asp Cys Cys Glu Lys Gln Glu Pro Asp Arg Asn Glu Cys Phe Leu Ala
                115                 120                 125

His Lys Asp Asp Asn Pro Gly Phe Pro Pro Leu Val Ala Pro Glu Pro
                130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Gln Gln Tyr Lys Gly Val Phe Ala Glu Cys
                180                 185                 190

Cys Gln Ala Ala Asp Lys Ala Ala Cys Leu Gly Pro Lys Ile Glu Ala
                195                 200                 205

Leu Arg Glu Lys Val Leu Leu Ser Ser Ala Lys Glu Arg Phe Lys Cys
         210                 215                 220

Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
                245                 250                 255

Lys Val Val Thr Asp Leu Thr Lys Val His Lys Glu Cys Cys His Gly
             260                 265                 270

Asp Leu Leu Glu Cys Ala Asp Asp Arg Ala Asp Leu Ala Lys Tyr Met
         275                 280                 285

Cys Glu Asn Gln Asp Ser Ile Ser Thr Lys Leu Lys Glu Cys Cys Asp
290                 295                 300

Lys Pro Val Leu Glu Lys Ser Gln Cys Leu Ala Glu Val Glu Arg Asp
305                 310                 315                 320

Glu Leu Pro Gly Asp Leu Pro Ser Leu Ala Ala Asp Phe Val Glu Asp
                325                 330                 335

Lys Glu Val Cys Lys Asn Tyr Gln Glu Ala Lys Asp Val Phe Leu Gly
             340                 345                 350

Thr Phe Leu Tyr Glu Tyr Ser Arg Arg His Pro Glu Tyr Ser Val Ser
         355                 360                 365

Leu Leu Leu Arg Leu Ala Lys Glu Tyr Glu Ala Thr Leu Glu Lys Cys
370                 375                 380

Cys Ala Thr Asp Asp Pro Pro Thr Cys Tyr Ala Lys Val Leu Asp Glu
385                 390                 395                 400

Phe Lys Pro Leu Val Asp Glu Pro Gln Asn Leu Val Lys Thr Asn Cys
                405                 410                 415

Glu Leu Phe Glu Lys Leu Gly Glu Tyr Gly Phe Gln Asn Ala Leu Leu
             420                 425                 430

Val Arg Tyr Thr Lys Lys Ala Pro Gln Val Ser Thr Pro Thr Leu Val
         435                 440                 445

Glu Val Ser Arg Lys Leu Gly Lys Val Gly Thr Lys Cys Cys Lys Lys
450                 455                 460

Pro Glu Ser Glu Arg Met Ser Cys Ala Asp Asp Phe Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Ser Glu Ser Leu Val Asn Arg Arg Pro Cys Phe
             500                 505                 510

Ser Gly Leu Glu Val Asp Glu Thr Tyr Val Pro Lys Glu Phe Asn Ala
         515                 520                 525

Glu Thr Phe Thr Phe His Ala Asp Leu Cys Thr Leu Pro Glu Ala Glu
530                 535                 540

Lys Gln Val Lys Gln Thr Ala Leu Val Glu Leu Leu Lys His Lys
545                 550                 555                 560

Pro Lys Ala Thr Asp Glu Gln Leu Lys Thr Val Met Gly Asp Phe Gly
                565                 570                 575

Ala Phe Val Glu Lys Cys Cys Ala Ala Glu Asn Lys Glu Gly Cys Phe
             580                 585                 590

Ser Glu Glu Gly Pro Lys Leu Val Ala Ala Gln Ala Ala Leu Val
         595                 600                 605

<210> SEQ ID NO 4
<211> LENGTH: 615
<212> TYPE: PRT

-continued

<213> ORGANISM: Gallus gallus

<400> SEQUENCE: 4

| | | | | | | | | | | | | | | |
|---|---|---|---|---|---|---|---|---|---|---|---|---|---|---|
| Met | Lys | Trp | Val | Thr | Leu | Ile | Ser | Phe | Ile | Phe | Leu | Phe | Ser | Ser | Ala |
| 1 | | | | 5 | | | | | 10 | | | | | 15 | |
| Thr | Ser | Arg | Asn | Leu | Gln | Arg | Phe | Ala | Arg | Asp | Ala | Glu | His | Lys | Ser |
| | | | 20 | | | | | 25 | | | | | 30 | | |
| Glu | Ile | Ala | His | Arg | Tyr | Asn | Asp | Leu | Lys | Glu | Glu | Thr | Phe | Lys | Ala |
| | | | | 35 | | | | | 40 | | | | | 45 | |
| Val | Ala | Met | Ile | Thr | Phe | Ala | Gln | Tyr | Leu | Gln | Arg | Cys | Ser | Tyr | Glu |
| | 50 | | | | | 55 | | | | | 60 | | | | |
| Gly | Leu | Ser | Lys | Leu | Val | Lys | Asp | Val | Val | Asp | Leu | Ala | Gln | Lys | Cys |
| 65 | | | | | 70 | | | | | 75 | | | | | 80 |
| Val | Ala | Asn | Glu | Asp | Ala | Pro | Glu | Cys | Ser | Lys | Pro | Leu | Pro | Ser | Ile |
| | | | | 85 | | | | | 90 | | | | | 95 | |
| Ile | Leu | Asp | Glu | Ile | Cys | Gln | Val | Glu | Lys | Leu | Arg | Asp | Ser | Tyr | Gly |
| | | | 100 | | | | | 105 | | | | | 110 | | |
| Ala | Met | Ala | Asp | Cys | Cys | Ser | Lys | Ala | Asp | Pro | Glu | Arg | Asn | Glu | Cys |
| | | | | 115 | | | | | 120 | | | | | 125 | |
| Phe | Leu | Ser | Phe | Lys | Val | Ser | Gln | Pro | Asp | Phe | Val | Gln | Pro | Tyr | Gln |
| | 130 | | | | | 135 | | | | | 140 | | | | |
| Arg | Pro | Ala | Ser | Asp | Val | Ile | Cys | Gln | Glu | Tyr | Gln | Asp | Asn | Arg | Val |
| 145 | | | | | 150 | | | | | 155 | | | | | 160 |
| Ser | Phe | Leu | Gly | His | Phe | Ile | Tyr | Ser | Val | Ala | Arg | Arg | His | Pro | Phe |
| | | | | 165 | | | | | 170 | | | | | 175 | |
| Leu | Tyr | Ala | Pro | Ala | Ile | Leu | Ser | Phe | Ala | Val | Asp | Phe | Glu | His | Ala |
| | | | 180 | | | | | 185 | | | | | 190 | | |
| Leu | Gln | Ser | Cys | Cys | Lys | Glu | Ser | Asp | Val | Gly | Ala | Cys | Leu | Asp | Thr |
| | | | | 195 | | | | | 200 | | | | | 205 | |
| Lys | Glu | Ile | Val | Met | Arg | Glu | Lys | Ala | Lys | Gly | Val | Ser | Val | Lys | Gln |
| | 210 | | | | | 215 | | | | | 220 | | | | |
| Gln | Tyr | Phe | Cys | Gly | Ile | Leu | Lys | Gln | Phe | Gly | Asp | Arg | Val | Phe | Gln |
| 225 | | | | | 230 | | | | | 235 | | | | | 240 |
| Ala | Arg | Gln | Leu | Ile | Tyr | Leu | Ser | Gln | Lys | Tyr | Pro | Lys | Ala | Pro | Phe |
| | | | | 245 | | | | | 250 | | | | | 255 | |
| Ser | Glu | Val | Ser | Lys | Phe | Val | His | Asp | Ser | Ile | Gly | Val | His | Lys | Glu |
| | | | 260 | | | | | 265 | | | | | 270 | | |
| Cys | Cys | Glu | Gly | Asp | Met | Val | Glu | Cys | Met | Asp | Asp | Met | Ala | Arg | Met |
| | | | | 275 | | | | | 280 | | | | | 285 | |
| Met | Ser | Asn | Leu | Cys | Ser | Gln | Gln | Asp | Val | Phe | Ser | Gly | Lys | Ile | Lys |
| | 290 | | | | | 295 | | | | | 300 | | | | |
| Asp | Cys | Cys | Glu | Lys | Pro | Ile | Val | Glu | Arg | Ser | Gln | Cys | Ile | Met | Glu |
| 305 | | | | | 310 | | | | | 315 | | | | | 320 |
| Ala | Glu | Phe | Asp | Glu | Lys | Pro | Ala | Asp | Leu | Pro | Ser | Leu | Val | Glu | Lys |
| | | | | 325 | | | | | 330 | | | | | 335 | |
| Tyr | Ile | Glu | Asp | Lys | Glu | Val | Cys | Lys | Ser | Phe | Glu | Ala | Gly | His | Asp |
| | | | 340 | | | | | 345 | | | | | 350 | | |
| Ala | Phe | Met | Ala | Glu | Phe | Val | Tyr | Glu | Tyr | Ser | Arg | Arg | His | Pro | Glu |
| | | | | 355 | | | | | 360 | | | | | 365 | |
| Phe | Ser | Ile | Gln | Leu | Ile | Met | Arg | Ile | Ala | Lys | Gly | Tyr | Glu | Ser | Leu |
| | 370 | | | | | 375 | | | | | 380 | | | | |
| Leu | Glu | Lys | Cys | Cys | Lys | Thr | Asp | Asn | Pro | Ala | Glu | Cys | Tyr | Ala | Asn |
| 385 | | | | | 390 | | | | | 395 | | | | | 400 |
| Ala | Gln | Glu | Gln | Leu | Asn | Gln | His | Ile | Lys | Glu | Thr | Gln | Asp | Val | Val |

```
                    405                 410                 415
Lys Thr Asn Cys Asp Leu Leu His Asp His Gly Glu Ala Asp Phe Leu
            420                 425                 430

Lys Ser Ile Leu Ile Arg Tyr Thr Lys Lys Met Pro Gln Val Pro Thr
            435                 440                 445

Asp Leu Leu Glu Thr Gly Lys Lys Met Thr Thr Ile Gly Thr Lys
    450                 455                 460

Cys Cys Gln Leu Gly Glu Asp Arg Arg Met Ala Cys Ser Glu Gly Tyr
465                 470                 475                 480

Leu Ser Ile Val Ile His Asp Thr Cys Arg Lys Gln Glu Thr Thr Pro
                485                 490                 495

Ile Asn Asp Asn Val Ser Gln Cys Cys Ser Gln Leu Tyr Ala Asn Arg
            500                 505                 510

Arg Pro Cys Phe Thr Ala Met Gly Val Asp Thr Lys Tyr Val Pro Pro
            515                 520                 525

Pro Phe Asn Pro Asp Met Phe Ser Phe Asp Glu Lys Leu Cys Ser Ala
            530                 535                 540

Pro Ala Glu Glu Arg Glu Val Gly Gln Met Lys Leu Leu Ile Asn Leu
545                 550                 555                 560

Ile Lys Arg Lys Pro Gln Met Thr Glu Glu Gln Ile Lys Thr Ile Ala
                565                 570                 575

Asp Gly Phe Thr Ala Met Val Asp Lys Cys Cys Lys Gln Ser Asp Ile
            580                 585                 590

Asn Thr Cys Phe Gly Glu Glu Gly Ala Asn Leu Ile Val Gln Ser Arg
            595                 600                 605

Ala Thr Leu Gly Ile Gly Ala
            610                 615

<210> SEQ ID NO 5
<211> LENGTH: 608
<212> TYPE: PRT
<213> ORGANISM: Macaca mulatta

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Asp Thr His Lys Ser Glu Val Ala
            20                  25                  30

His Arg Phe Lys Asp Leu Gly Glu Glu His Phe Lys Gly Leu Val Leu
        35                  40                  45

Val Ala Phe Ser Gln Tyr Leu Gln Gln Cys Pro Phe Glu Glu His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Leu Val Arg Pro Glu Val
    130                 135                 140

Asp Val Met Cys Thr Ala Phe His Asp Asn Glu Ala Thr Phe Leu Lys
145                 150                 155                 160

Lys Tyr Leu Tyr Glu Val Ala Arg Arg His Pro Tyr Phe Tyr Ala Pro
```

```
                    165                 170                 175
Glu Leu Leu Phe Phe Ala Ala Arg Tyr Lys Ala Phe Ala Glu Cys
                180                 185                 190
Cys Gln Ala Ala Asp Lys Ala Ala Cys Leu Leu Pro Lys Leu Asp Glu
            195                 200                 205
Leu Arg Asp Glu Gly Lys Ala Ser Ser Ala Lys Gln Arg Leu Lys Cys
        210                 215                 220
Ala Ser Leu Gln Lys Phe Gly Asp Arg Ala Phe Lys Ala Trp Ala Val
225                 230                 235                 240
Ala Arg Leu Ser Gln Lys Phe Pro Lys Ala Glu Phe Ala Glu Val Ser
                245                 250                 255
Lys Leu Val Thr Asp Leu Thr Lys Val His Thr Glu Cys Cys His Gly
                260                 265                 270
Asp Leu Leu Glu Cys Ala Asp Asp Arg Ala Asp Leu Ala Lys Tyr Met
            275                 280                 285
Cys Glu Asn Gln Asp Ser Ile Ser Ser Lys Leu Lys Glu Cys Cys Asp
        290                 295                 300
Lys Pro Leu Leu Glu Lys Ser His Cys Leu Ala Glu Val Glu Asn Asp
305                 310                 315                 320
Glu Met Pro Ala Asp Leu Pro Ser Leu Ala Ala Asp Tyr Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Met
        355                 360                 365
Leu Leu Leu Arg Leu Ala Lys Ala Tyr Glu Ala Thr Leu Glu Lys Cys
        370                 375                 380
Cys Ala Ala Ala Asp Pro His Glu Cys Tyr Ala Lys Val Phe Asp Glu
385                 390                 395                 400
Phe Gln Pro Leu Val Glu Glu Pro Gln Asn Leu Val Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ala Lys Cys Cys Lys Leu
        450                 455                 460
Pro Glu Ala Lys Arg Met Pro Cys Ala Glu Asp Tyr Leu Ser Val Val
465                 470                 475                 480
Leu Asn Arg Leu Cys Val Leu His Glu Lys Thr Pro Val Ser Glu Lys
                485                 490                 495
Val Thr Lys Cys Cys Thr Glu Ser Leu Val Asn Arg Arg Pro Cys Phe
            500                 505                 510
Ser Ala Leu Glu Leu Asp Glu Ala Tyr Val Pro Lys Ala Phe Asn Ala
        515                 520                 525
Glu Thr Phe Thr Phe His Ala Asp Met Cys Thr Leu Ser Glu Lys Glu
        530                 535                 540
Lys Gln Val Lys Lys Gln Thr Ala Leu Val Glu Leu Val Lys His Lys
545                 550                 555                 560
Pro Lys Ala Thr Lys Glu Gln Leu Lys Gly Val Met Asp Asn Phe Ala
                565                 570                 575
Ala Phe Val Glu Lys Cys Cys Lys Ala Asp Asp Lys Glu Ala Cys Phe
            580                 585                 590
```

-continued

Ala Glu Glu Gly Pro Lys Phe Val Ala Ser Gln Ala Ala Leu Ala
         595                 600                 605

<210> SEQ ID NO 6
<211> LENGTH: 607
<212> TYPE: PRT
<213> ORGANISM: Bos taurus

<400> SEQUENCE: 6

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
            85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
            115                 120                 125

His Lys Asp Asp Ser Pro Asp Leu Pro Lys Leu Lys Pro Asp Pro Asn
            130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
            165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
            195                 200                 205

Arg Glu Lys Val Leu Thr Ser Ser Ala Arg Gln Arg Leu Arg Cys Ala
            210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
            245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
            275                 280                 285

Asp Asn Gln Asp Thr Ile Ser Ser Lys Leu Lys Glu Cys Cys Asp Lys
            290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
            325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Glu Cys Cys
        370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
                420                 425                 430

Arg Tyr Thr Arg Lys Val Pro Gln Val Ser Thr Pro Thr Leu Val Glu
                435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Val Pro Lys Ala Phe Asp Glu Lys
                515                 520                 525

Leu Phe Thr Phe His Ala Asp Ile Cys Thr Leu Pro Asp Thr Glu Lys
                530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
                580                 585                 590

Val Glu Gly Pro Lys Leu Val Val Ser Thr Gln Thr Ala Leu Ala
                595                 600                 605

<210> SEQ ID NO 7
<211> LENGTH: 608
<212> TYPE: PRT
<213> ORGANISM: Rattus norvegicus

<400> SEQUENCE: 7

Met Lys Trp Val Thr Phe Leu Leu Leu Phe Ile Ser Gly Ser Ala
1               5                   10                  15

Phe Ser Arg Gly Val Phe Arg Arg Glu Ala His Lys Ser Glu Ile Ala
                20                  25                  30

His Arg Phe Lys Asp Leu Gly Glu Gln His Phe Lys Gly Leu Val Leu
                35                  40                  45

Ile Ala Phe Ser Gln Tyr Leu Gln Lys Cys Pro Tyr Glu Glu His Ile
        50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
                100                 105                 110

Asp Cys Cys Ala Lys Gln Glu Pro Glu Arg Asn Glu Cys Phe Leu Gln
                115                 120                 125

His Lys Asp Asp Asn Pro Asn Leu Pro Pro Phe Gln Arg Pro Glu Ala
        130                 135                 140

-continued

```
Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

Cys Thr Glu Ser Asp Lys Ala Ala Cys Leu Thr Pro Lys Leu Asp Ala
        195                 200                 205

Val Lys Glu Lys Ala Leu Val Ala Ala Val Arg Gln Arg Met Lys Cys
210                 215                 220

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
                245                 250                 255

Lys Leu Ala Thr Asp Val Thr Lys Ile Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Ala Cys Cys Asp
290                 295                 300

Lys Pro Val Leu Gln Lys Ser Gln Cys Leu Ala Glu Thr Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
370                 375                 380

Cys Ala Glu Gly Asp Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Glu Leu Tyr Glu Lys Leu Gly Glu Tyr Gly Phe Gln Asn Ala Val Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Asp Lys Glu
530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575
```

```
Gln Phe Val Asp Lys Cys Cys Lys Ala Ala Asp Lys Asp Asn Cys Phe
                580                 585                 590
Ala Thr Glu Gly Pro Asn Leu Val Ala Arg Ser Lys Glu Ala Leu Ala
            595                 600                 605

<210> SEQ ID NO 8
<211> LENGTH: 608
<212> TYPE: PRT
<213> ORGANISM: Felis catus

<400> SEQUENCE: 8

Met Lys Trp Val Thr Phe Ile Ser Leu Leu Leu Phe Ser Ser Ala
1               5                   10                  15
Tyr Ser Arg Gly Val Thr Arg Arg Glu Ala His Gln Ser Glu Ile Ala
                20                  25                  30
His Arg Phe Asn Asp Leu Gly Glu Glu His Phe Arg Gly Leu Val Leu
            35                  40                  45
Val Ala Phe Ser Gln Tyr Leu Gln Gln Cys Pro Phe Glu Asp His Val
        50                  55                  60
Lys Leu Val Asn Glu Val Thr Glu Phe Ala Lys Gly Cys Val Ala Asp
65                  70                  75                  80
Gln Ser Ala Ala Asn Cys Glu Lys Ser Leu His Glu Leu Leu Gly Asp
                85                  90                  95
Lys Leu Cys Thr Val Ala Ser Leu Arg Asp Lys Tyr Gly Glu Met Ala
            100                 105                 110
Asp Cys Cys Glu Lys Lys Glu Pro Glu Arg Asn Glu Cys Phe Leu Gln
        115                 120                 125
His Lys Asp Asp Asn Pro Gly Phe Gly Gln Leu Val Thr Pro Glu Ala
130                 135                 140
Asp Ala Met Cys Thr Ala Phe His Glu Asn Glu Gln Arg Phe Leu Gly
145                 150                 155                 160
Lys Tyr Leu Tyr Glu Ile Ala Arg Arg His Pro Tyr Phe Tyr Ala Pro
                165                 170                 175
Glu Leu Leu Tyr Tyr Ala Glu Glu Tyr Lys Gly Val Phe Thr Glu Cys
            180                 185                 190
Cys Glu Ala Ala Asp Lys Ala Ala Cys Leu Thr Pro Lys Val Asp Ala
        195                 200                 205
Leu Arg Glu Lys Val Leu Ala Ser Ser Ala Lys Glu Arg Leu Lys Cys
210                 215                 220
Ala Ser Leu Gln Lys Phe Gly Glu Arg Ala Phe Lys Ala Trp Ser Val
225                 230                 235                 240
Ala Arg Leu Ser Gln Lys Phe Pro Lys Ala Glu Phe Ala Glu Ile Ser
                245                 250                 255
Lys Leu Val Thr Asp Leu Ala Lys Ile His Lys Glu Cys Cys His Gly
            260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Thr Lys Leu Lys Glu Cys Cys Gly
290                 295                 300
Lys Pro Val Leu Glu Lys Ser His Cys Ile Ser Glu Val Glu Arg Asp
305                 310                 315                 320
Glu Leu Pro Ala Asp Leu Pro Pro Leu Ala Val Asp Phe Val Glu Asp
                325                 330                 335
Lys Glu Val Cys Lys Asn Tyr Gln Glu Ala Lys Asp Val Phe Leu Gly
            340                 345                 350
```

```
Thr Phe Leu Tyr Glu Tyr Ser Arg Arg His Pro Glu Tyr Ser Val Ser
            355                 360                 365

Leu Leu Leu Arg Leu Ala Lys Glu Tyr Glu Ala Thr Leu Glu Lys Cys
        370                 375                 380

Cys Ala Thr Asp Asp Pro Pro Ala Cys Tyr Ala His Val Phe Asp Glu
385                 390                 395                 400

Phe Lys Pro Leu Val Glu Glu Pro His Asn Leu Val Lys Thr Asn Cys
                405                 410                 415

Glu Leu Phe Glu Lys Leu Gly Glu Tyr Gly Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Ser Leu Gly Lys Val Gly Ser Lys Cys Cys Thr His
    450                 455                 460

Pro Glu Ala Glu Arg Leu Ser Cys Ala Glu Asp Tyr Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Thr Glu Ser Leu Val Asn Arg Arg Pro Cys Phe
            500                 505                 510

Ser Ala Leu Gln Val Asp Glu Thr Tyr Val Pro Lys Glu Phe Ser Ala
        515                 520                 525

Glu Thr Phe Thr Phe His Ala Asp Leu Cys Thr Leu Pro Glu Ala Glu
    530                 535                 540

Lys Gln Ile Lys Lys Gln Ser Ala Leu Val Glu Leu Leu Lys His Lys
545                 550                 555                 560

Pro Lys Ala Thr Glu Glu Gln Leu Lys Thr Val Met Gly Asp Phe Gly
                565                 570                 575

Ser Phe Val Asp Lys Cys Cys Ala Ala Glu Asp Lys Glu Ala Cys Phe
            580                 585                 590

Ala Glu Glu Gly Pro Lys Leu Val Ala Ala Gln Ala Ala Leu Ala
        595                 600                 605

<210> SEQ ID NO 9
<211> LENGTH: 606
<212> TYPE: PRT
<213> ORGANISM: Xenopus laevis

<400> SEQUENCE: 9

Met Lys Trp Ile Thr Leu Ile Cys Leu Leu Ile Ser Ser Thr Leu Ile
1               5                   10                  15

Glu Ser Arg Ile Ile Phe Lys Arg Asp Thr Asp Val Asp His His Lys
            20                  25                  30

His Ile Ala Asp Met Tyr Asn Leu Leu Thr Glu Arg Thr Phe Lys Gly
        35                  40                  45

Leu Thr Leu Ala Ile Val Ser Gln Asn Leu Gln Lys Cys Ser Leu Glu
    50                  55                  60

Glu Leu Ser Lys Leu Val Asn Glu Ile Asn Asp Phe Ala Lys Ser Cys
65                  70                  75                  80

Thr Gly Asn Asp Lys Thr Pro Glu Cys Glu Lys Pro Ile Gly Thr Leu
                85                  90                  95

Phe Tyr Asp Lys Leu Cys Ala Asp Pro Lys Val Gly Val Asn Tyr Glu
            100                 105                 110

Trp Ser Lys Glu Cys Cys Ser Lys Gln Asp Pro Glu Arg Ala Gln Cys
        115                 120                 125
```

-continued

Phe Arg Ala His Arg Val Phe Glu His Asn Pro Val Arg Pro Lys Pro
        130                 135                 140

Glu Glu Thr Cys Ala Leu Phe Lys Glu His Pro Asp Asp Leu Leu Ser
145                 150                 155                 160

Ala Phe Ile His Glu Glu Ala Arg Asn His Pro Asp Leu Tyr Pro Pro
                165                 170                 175

Ala Val Leu Leu Leu Thr Gln Gln Tyr Gly Lys Leu Val Glu His Cys
            180                 185                 190

Cys Glu Glu Glu Asp Lys Asp Lys Cys Phe Ala Glu Lys Met Lys Glu
        195                 200                 205

Leu Met Lys His Ser His Ser Ile Glu Asp Lys Gln Lys His Phe Cys
    210                 215                 220

Trp Ile Val Asn Asn Tyr Pro Glu Arg Val Ile Lys Ala Leu Asn Leu
225                 230                 235                 240

Ala Arg Val Ser His Arg Tyr Pro Lys Pro Asp Phe Lys Leu Ala His
                245                 250                 255

Lys Phe Thr Glu Glu Thr Thr His Phe Ile Lys Asp Cys Cys His Gly
            260                 265                 270

Asp Met Phe Glu Cys Met Thr Glu Arg Leu Glu Leu Ser Glu His Thr
        275                 280                 285

Cys Gln His Lys Asp Glu Leu Ser Thr Lys Leu Glu Lys Cys Cys Asn
    290                 295                 300

Leu Pro Leu Leu Glu Arg Thr Tyr Cys Ile Val Thr Leu Glu Asn Asp
305                 310                 315                 320

Asp Val Pro Ala Glu Leu Ser Lys Pro Ile Thr Glu Phe Thr Glu Asp
                325                 330                 335

Pro His Val Cys Glu Lys Tyr Ala Glu Asn Lys Ser Phe Leu Glu Ile
            340                 345                 350

Ser Pro Trp Gln Ser Gln Glu Thr Pro Glu Leu Ser Glu Gln Phe Leu
        355                 360                 365

Leu Gln Ser Ala Lys Glu Tyr Glu Ser Leu Leu Asn Lys Cys Cys Phe
    370                 375                 380

Ser Asp Asn Pro Pro Glu Cys Tyr Lys Asp Gly Ala Asp Arg Phe Met
385                 390                 395                 400

Asn Glu Ala Lys Glu Arg Phe Ala Tyr Leu Lys Gln Asn Cys Asp Ile
                405                 410                 415

Leu His Glu His Gly Glu Tyr Leu Phe Glu Asn Glu Leu Leu Ile Arg
            420                 425                 430

Tyr Thr Lys Lys Met Pro Gln Val Ser Asp Glu Thr Leu Ile Gly Ile
        435                 440                 445

Ala His Gln Met Ala Asp Ile Gly Glu His Cys Cys Ala Val Pro Glu
    450                 455                 460

Asn Gln Arg Met Pro Cys Ala Glu Gly Asp Leu Thr Ile Leu Ile Gly
465                 470                 475                 480

Lys Met Cys Glu Arg Gln Lys Lys Thr Phe Ile Asn Asn His Val Ala
                485                 490                 495

His Cys Cys Thr Asp Ser Tyr Ser Gly Met Arg Ser Cys Phe Thr Ala
            500                 505                 510

Leu Gly Pro Asp Glu Asp Tyr Val Pro Pro Val Thr Asp Thr
        515                 520                 525

Phe His Phe Asp Asp Lys Ile Cys Thr Ala Asn Asp Lys Glu Lys Gln
    530                 535                 540

His Ile Lys Gln Lys Phe Leu Val Lys Leu Ile Lys Val Ser Pro Lys

-continued

```
            545                 550                 555                 560

Leu Glu Lys Asn His Ile Asp Glu Trp Leu Leu Glu Phe Leu Lys Met
                565                 570                 575

Val Gln Lys Cys Cys Thr Ala Asp Glu His Gln Pro Cys Phe Asp Thr
                580                 585                 590

Glu Lys Pro Val Leu Ile Glu His Cys Gln Lys Leu His Pro
                595                 600                 605
```